US012594389B2

(12) United States Patent
Troili et al.

(10) Patent No.: US 12,594,389 B2
(45) Date of Patent: *Apr. 7, 2026

(54) NON-INVASIVE ESTIMATION OF HEMODYNAMIC PARAMETERS DURING MECHANICAL VENTILATION

(71) Applicant: MAQUET CRITICAL CARE AB, Solna (SE)

(72) Inventors: Carl-Erik Troili, Danderyd (SE); Tomas Westerlund, Sollentuna (SE)

(73) Assignee: MAQUET CRITICAL CARE AB, Solna (SE)

( * ) Notice: Subject to any disclaimer, the term of this patent is extended or adjusted under 35 U.S.C. 154(b) by 1212 days.

This patent is subject to a terminal disclaimer.

(21) Appl. No.: 17/250,277

(22) PCT Filed: Jun. 25, 2019

(86) PCT No.: PCT/SE2019/050612

§ 371 (c)(1),
(2) Date: Dec. 23, 2020

(87) PCT Pub. No.: WO2020/009639

PCT Pub. Date: Jan. 9, 2020

(65) Prior Publication Data

US 2021/0260313 A1 Aug. 26, 2021

(30) Foreign Application Priority Data

Jul. 6, 2018 (WO) ................ PCT/SE2018/050748

(51) Int. Cl.
*A61M 16/00* (2006.01)
*A61B 5/0205* (2006.01)
(Continued)

(52) U.S. Cl.
CPC ....... *A61M 16/0003* (2014.02); *A61B 5/0205* (2013.01); *A61B 5/02125* (2013.01);
(Continued)

(58) Field of Classification Search
None
See application file for complete search history.

(56) References Cited

U.S. PATENT DOCUMENTS

2016/0066801 A1 3/2016 Kahlert et al.
2016/0345844 A1 12/2016 McCombie et al.
(Continued)

FOREIGN PATENT DOCUMENTS

CN 107095659 8/2017
WO 2016/153406 A1 9/2016

OTHER PUBLICATIONS

Contal et al. Pulse transit time as a measure of respiratory effort under noninvasive ventilation Eur Respir J 2013; 41: 346-353 (Year: 2013).*

*Primary Examiner* — Jay B Shah
(74) *Attorney, Agent, or Firm* — Fay Kaplun & Marcin, LLP

(57) ABSTRACT

The present disclosure relates to a method for non-invasive determination of a hemodynamic parameter of a mechanically ventilated subject (3) based on a point in time ($t_{hb}$) of a heartbeat of the subject and an arrival point in time ($t_{arr\_pulm}$, $t_{arr\_sys}$) at which a blood pressure pulse caused by the heartbeat reaches a point of arrival in the circulatory system of the subject. The method comprises the steps of measuring (S41) a respiratory pressure and/or a respiratory flow, and determining (S43) the point in time ($t_{hb}$) of the heartbeat from a change in the measured respiratory pressure
(Continued)

and/or the respiratory flow resulting from a physical impact of the heart on the lungs of the subject (3) during the heartbeat.

25 Claims, 4 Drawing Sheets

(51) Int. Cl.
*A61B 5/021* (2006.01)
*A61B 5/087* (2006.01)

(52) U.S. Cl.
CPC .......... *A61B 5/087* (2013.01); *A61M 16/022* (2017.08); *A61M 2016/0027* (2013.01); *A61M 2016/003* (2013.01); *A61M 2230/30* (2013.01); *A61M 2230/40* (2013.01)

(56) References Cited

U.S. PATENT DOCUMENTS

2017/0238815 A1 8/2017 Luxon et al.
2018/0140252 A1 5/2018 Luxon et al.

* cited by examiner

NON-INVASIVE ESTIMATION OF HEMODYNAMIC PARAMETERS DURING MECHANICAL VENTILATION

TECHNICAL FIELD

The present invention relates to a method, a computer program and a ventilation system for non-invasive estimation of a hemodynamic parameter during mechanical ventilation of a subject.

BACKGROUND

During mechanical ventilation there is a demand for monitoring the physiological state of the ventilated patient. Electrocardiogram (ECG) measurement systems, blood pressure sensors and pulse oximeters are examples of medical devices that are widely known and used to monitor the cardiovascular function of mechanically ventilated patients.

Monitoring of hemodynamic parameters relating to the pulmonary and/or the systemic circulation of the ventilated patient may be important in the assessment of the patient's cardiovascular function. For instance, it may be desirable to monitor one or more hemodynamic parameters selected from the group consisting of systemic blood pressure (SBP), pulmonary blood pressure (PBP), systemic cardiac output (SCO), pulmonary cardiac output (PCO), and intracardiac shunt.

Most known methods for determination of these and other hemodynamic parameters are unsuitable for use during mechanical ventilation due to their invasive and complicated nature, their inability of being performed continuously, and/or their need for additional equipment not normally available at the bedside of mechanically ventilated patients.

An example of a non-invasive technique for SBP determination is the esCCO technique developed by Nihon Koden and described on https://eu.nihonkohden.com/en/innovativetechnologies/escco (2019-04-17). The principle of esCCO is based on the inverse correlation between stroke volume (SV) and systemic pulse transit time (PTT), sometimes referred to as pulse wave transit time (PWTT). According to this principle, an estimate ("esCCO") of the combined cardiac output (i.e the sum of the outputs of the right and left sides of the heart) of a patient may be calculated from the following equation:

$$esCCO=K\times(\alpha\times PTT+\beta)\times HR,$$

where $\alpha$ is a constant, K and $\beta$ are constants that need to be individualized for each patient and may be estimated based on patient characteristics, such as patient length, weight, sex, etc., and HR is the heartrate of the patient.

By determining the systemic PTT from measured electrocardiogram (ECG) and peripheral capillary oxygen saturation (SpO2) signals, e.g. as the time measured from the ECG R-wave peak to the rise point of SpO2 pulse wave, the esCCO technique allows the SCO to be determined non-invasively using nothing but an ECG sensor and an SpO2 sensor.

The systemic PTT may also be used for non-invasive and cuff-free determination of SBP, as described e.g. in Wang et al., "Cuff-free blood pressure estimation using pulse transit time and heart rate", 2014 12$^{th}$ International Conference on Signal Processing (ICSP), pp. 115-118, 2014. This non-invasive and cuff-free technique for blood pressure determination allows the systemic blood pressure of a patient to be calculated from the following equation:

$$SBP=-\frac{2}{\propto}\cdot\ln PTT+\frac{\ln\frac{2r\rho L^2}{hE_0}}{\alpha},$$

where $\alpha$ is a constant, r is the inner radius of the blood vessel, $\rho$ is the blood density, L is the vessel length, h is the vessel wall thickness, and $E_0$ is the zero-pressure elastic modulus of the vessel wall. Consequently, ECG measurements and SpO2 measurements may be used for non-invasive determination of systemic cardiac output and systemic blood pressure.

A disadvantage of the above described techniques is that they cannot be readily used for determination of PCO and PBP since a PTT of a blood pressure pulse propagating along the pulmonary arteries of a patient cannot easily be determined non-invasively. In order to determine PTT, one must be able to determine the point in time of arrival of the blood pressure pulse at a point of measurement, which is a non-trivial task along the pulmonary arteries of a patient.

Another disadvantage of the above described techniques is that they require use of an ECG sensor for detecting the point in time of the heartbeat generating the blood pressure pulse for which the PTT is to be determined. Although ECG monitoring is commonplace during mechanical ventilation, it would be desirable to be able to determine hemodynamic parameters such as SBP, SCO, PBP and PCO without the need for ECG sensors or other peripheral equipment.

An example of a non-invasive technique for PBP determination is the ultrasound-based technique disclosed by Micah R Fisher et al, "Accuracy of Doppler Echocardiography in the Hemodynamic Assessment of Pulmonary Hypertension", American Journal of Respiratory and Critical Care Medicine, Vol. 179, No. 7 (2009), pp. 615-621. According to this technique, ultrasound is used to compare a flow of blood going in the direction of the lungs of a patient with a blood flow leaking back towards the patient's heart. The comparison may be used to estimate the pulmonary blood flow of the patient. This technique requires additional equipment in form of ultrasound transducers and is dependent on qualified personnel to perform the measurements.

Another non-invasive technique for PBP determination employs Doppler echocardiography to determine the time required (pulse transit time, PTT) for a blood pressure pulse to propagate between two locations along the pulmonary artery. This technique requires Doppler echocardiography equipment and a rather complex setup with at least two points of measurement.

Yet another example of a non-invasive technique for PBP determination is disclosed in "Non-invasive monitoring of pulmonary artery pressure at the bedside", Conf Proc IEEE Eng Med Biol Soc. 2016 August; 2016:4236-4239, doi: 10.1109/EMBC.2016.7591662, by Proenca M et al. This technique employs electrical impedance tomography (EIT), which is another medical imaging technique, in order to monitor the pulmonary blood pressure of a patient continuously.

Non-invasive techniques based on magnetic resonance (MR) imaging techniques have also been proposed for the assessment of pulmonary arterial stiffness or PBP estimation. For example, "Assessment of proximal pulmonary arterial stiffness using magnetic resonance imaging: effects of technique, age and exercise", BMJ Open Respir Res. 2016 Oct. 7; 3(1):e000149. eCollection 2016, by Weir-McCall J R et al. discloses an MR-based technique for determining pulmonary pulse wave velocity (PWV).

Yet another example of a non-invasive method for PBP determination is described in US 2016/0066801. The method is an acoustic method employing the forced oscillation technique (FOT), as further described e.g. in "The forced oscillation technique in clinical practice: methodology, recommendations and future developments", E. Oostveen et al., European Respiratory Journal, 2003; 22:1026-1041.

The method disclosed in US 2016/0066801 involves the use of a phonocardiograph or ECG equipment for determining a pulse start time, T1, indicating the time of a heartbeat of a patient, and the use of FOT equipment for determining a pulse arrival time, T2, at the alveoli of the lungs of the patient. The pulmonary PTT of the pulse may then be determined from T1 and T2 and used to calculate the PBP of the patient, e.g. based on a known relationship between pulse wave velocity (PWV) and blood pressure, such as the Moens-Korteweg-relation. The FOT for determining the pulse arrival time at the alveoli of the lungs of the patient involves the generation of pressure oscillations by means of a loudspeaker, and the application of such pressure oscillations into the airways of the patient at a frequency that is higher than the natural breathing frequency of the patient. The FOT further involves the registration of flow and pressure signals close to the airway opening of the patient by means of a pneumotachograph and a pressure transducer, respectively. The complex relationship between applied pressure and resulting flow, called impedance (Zrs), is determined by the mechanical properties of the airways, the lung tissue and the chest wall, and is dependent on the frequency of the applied pressure oscillations. By studying the frequency dependent behaviour of Zrs and, in particular, by identifying a change of Zrs at the arrival of the pulmonary blood pulse wave, the pulse arrival time, T2, can be determined.

Although enabling determination of a pulmonary PTT along the pulmonary arteries of a patient, and thus enabling non-invasive determination of PBP, the method disclosed in US 2016/0066801 suffers from the drawback of requiring the use of FOT equipment for determination of the time of arrival of the blood pressure pulse at the lungs of the patient, and the use of a phonocardiograph or ECG equipment for determining the point in time of the heartbeat of the patient.

Due to the above mentioned drawbacks associated with the prior art, there is a need for a non-invasive technique for estimation of hemodynamic parameters such as SBP, SCO, PBP and PCO, which technique requires a minimum of peripheral equipment and is readily available at the bedside of a mechanically ventilated patient.

SUMMARY

It is an object of the disclosure to present a technique for non-invasive estimation of a hemodynamic parameter of a mechanically ventilated patient, which technique solves or at least mitigates one or more of the above-mentioned problems associated with the prior art.

It is another object of the disclosure to present a technique for non-invasive estimation of a hemodynamic parameter of a mechanically ventilated patient, which technique is readily available at the bedside of the mechanically ventilated patient.

It is a particular object of the disclosure to present a technique for non-invasive estimation of a hemodynamic parameter of a mechanically ventilated patient, which technique can be used without the need for additional equipment or medical devices not normally available at the bedside of mechanically ventilated patients.

Yet further, it is an object of the disclosure to present a technique for non-invasive estimation of a hemodynamic parameter of a mechanically ventilated patient, which technique allows the hemodynamic parameter to be monitored continuously.

In particular, the present disclosure aims at presenting an improved or at least alternative technique for automatic and non-invasive determination of hemodynamic parameters relating to the pulmonary or systemic circulation of a mechanically ventilated patient.

These and other objects are achieved in accordance with the present disclosure by a method, a computer program and a ventilation system as defined by the appended claims.

According to an aspect of the present disclosure, there is provided a method for non-invasive determination of a hemodynamic parameter of a mechanically ventilated subject based on a point in time, $t_{hb}$, of a heartbeat of the subject and an arrival point in time at which a blood pressure pulse caused by the heartbeat reaches a point of arrival in the circulatory system of the subject. The method comprises the steps of measuring a respiratory pressure and/or a respiratory flow, and determining $t_{hb}$ from a change in the measured respiratory pressure and/or the respiratory flow resulting from a physical impact of the heart on the lungs of the subject during the heartbeat, i.e. from a heartbeat-induced cardiogenic oscillation in either or both of the measured respiratory pressure and the measured respiratory flow.

The hemodynamic parameter may, for instance, be any of a pulmonary cardiac output (PCO), a pulmonary blood pressure (PBP), a systemic cardiac output (SCO) or a systemic blood pressure (SBP). The point in time of the heartbeat, $t_{hb}$, and the arrival point in time of the blood pressure pulse may be used to calculate a pulse transit time (PTT) of the blood pressure pulse when propagating along the systemic or pulmonary circulatory system of the ventilated subject. PCO, PBP, SCO and SBP may then be estimated from the pulmonary or systemic PTT based on any of the above mentioned relationships for systemic cardiac output and systemic blood pressure.

An advantage of determining the from a change in the measured respiratory pressure and/or the respiratory flow is that no other sensors than pressure and/or flow sensors normally existing in a ventilation system are required for the determination. For instance, in contrast to the FOT approach described in US 2016/0066801, no phonocardiograph or ECG equipment is needed for determining the point in time of the heartbeat.

The point in time of the heartbeat, $t_{hb}$ may be determined from a change in magnitude of the measured respiratory pressure and/or the measured respiratory flow. For example, $t_{hb}$ may be determined as the point in time at which the measured respiratory pressure and/or the measured respiratory flow reaches a threshold value.

Alternatively, $t_{hb}$ may be determined by analysing the curvature of a respiratory pressure curve and/or a respiratory flow curve, representing the change over time of the measured respiratory pressure and the measured respiratory flow, respectively. For example, $t_{hb}$ may be determined based on a change in a first and/or second order derivative with respect to time of the respiratory pressure curve and/or the respiratory flow curve. This is advantageous in that the first and/or second order derivative of the respiratory pressure curve and/or the respiratory flow curve may be affected to a greater extent than the amplitudes of the respiratory pressure curve and the respiratory flow curve at the time of the heartbeat. Consequently, studying changes in the first and/or second order derivative may provide a more precise and/or robust estimation of the time of the heartbeat.

The method may further comprise a step of estimating a time window for the heartbeat based on at least one parameter indicative of an approximate point in time of the heartbeat, and determining $t_{hb}$ based on the respiratory pressure and/or respiratory flow measured during the estimated time window. This may prevent fluctuations in the measured respiratory pressure and/or flow not caused by the heartbeat from being mistaken for heartbeat-induced cardiogenic oscillations, and so makes the method more robust.

The time window for the heartbeat may be estimated from any parameter indicative of the approximate point in time of the heartbeat, including but not limited to

- the determined arrival point in time of the blood pressure pulse to the point of arrival in the circulatory system of the subject;
- the point(s) in time of one or more previous heartbeats;
- the point(s) in time of arrival at the point of arrival of one or more previous blood pressure pulses generated by the one or more previous heartbeats;
- blood oxygenation data relating to oxygenation of blood in a body part at a known or assumable distance from the heart of the subject, and
- systemic blood pressure data relating to a systemic blood pressure measured in a body part at a known or assumable distance from the heart of the subject.

In particular, it may be advantageous to use blood oxygenation data in the estimation of the time window for the heartbeat.

Heartbeat-induced changes in the measured respiratory pressure and/or flow may sometimes be difficult to identify. Therefore, estimating a time window for the heartbeat and searching for the heartbeat only within said time window, as described above, may be desired in order to be able to identify the point in time of the heartbeat, $t_{hb}$, with a sufficient degree of certainty.

For example, the estimated time window for the heartbeat may be determined based on a point in time of a plurality of previously detected heartbeats. In one example, the time window may be determined based on the point in time of a preceding heartbeat and a heartrate of the subject, calculated based on the points in time of a plurality of preceding heartbeats. Additionally, a set respiration rate (RR) of the ventilated subject may be used to more reliably and/or more accurately estimate a time window for the heartbeat.

Alternatively or in addition, the estimated time window for the heartbeat may be determined retroactively based on sensor data indicative of the heartbeat itself. For example, the estimated time window for the heartbeat may be determined retroactively based on the determined arrival point in time of the blood pressure pulse to the point of arrival in the circulatory system of the subject. The determined arrival point in time may be used together with an uncertainty associated with the determination of the arrival point in time to set the boundaries of the estimated time window for the heartbeat. This type of retroactive determination of a time window for the heartbeat may be particularly advantageous in situations where the arrival point in time of the blood pressure pulse to the point of arrival in the circulatory system of the subject is more easily detectable than point in time, $t_{hb}$, of the heartbeat.

In one example, the time window for the heartbeat may be determined retroactively based on determination of a point in time of arrival, $t_{arr\_pulm}$, of a blood pressure pulse to the lungs of the ventilated subject, which point in time of arrival is determined based on a change in the measured respiratory pressure and/or the measured respiratory flow resulting from a change in a lung volume of the subject caused by the arrival of the blood pressure pulse to the lungs. The determined $t_{arr\_pulm}$ may be used together with an uncertainty associated with the determination of $t_{arr\_pulm}$ to set the boundaries of the estimated time window for the heartbeat. This type of retroactive determination of a time window for the heartbeat may be particularly advantageous in situations where $t_{arr\_pulm}$ is more easily detectable from the measured respiratory pressure and/or flow than $t_{hb}$.

In another example, the time window for the heartbeat may be determined retroactively based on blood oxygenation measurements. The blood oxygenation measurements may be obtained e.g. by a pulse oximeter attached to a body part of the ventilated subject, whereby the time window for the heartbeat may be determined based on a point in time of a change in blood oxygenation, registered by the pulse oximeter. The point in time of change in blood oxygenation may, together with an uncertainty associated with the determination thereof, be used to set the boundaries of the estimated time window for the heartbeat. In alternative to a pulse oximeter, a sphygmomanometer (i.e. a cuff-based blood pressure monitor) for measuring systemic blood pressure may be used to determine the point in time at which a systemic blood pressure pulse following a heartbeat reaches the point of measurement. In accordance with the above described principles, the point in time at which the systemic blood pressure pulse reaches the point of measurement can be used to retroactively estimate a time window for the heartbeat.

The point in time of arrival of the blood pressure pulse to the point of arrival in the circulatory system of the ventilated subject may be determined in different ways, depending on the hemodynamic parameter that is to be determined.

For instance, if the hemodynamic parameter is a hemodynamic parameter relating to the pulmonary circulatory system of the subject, such as PBP or PCO, the hemodynamic parameter may be determined based on a pulmonary pulse transit time ($PTT_{pulm}$) of a blood pressure pulse propagating along the pulmonary artery of the ventilated subject. In this case, the point in time of arrival of the blood pressure pulse may be determined as a point in time of arrival, $t_{arr\_pulm}$, of the blood pressure pulse to the lungs of the ventilated subject. The point in time of arrival, $t_{arr\_pulm}$, of the blood pressure pulse to the lungs of the ventilated subject may be determined based on a change in the measured respiratory pressure and/or the measured respiratory flow resulting from a change in a lung volume of the subject caused by the arrival of the blood pressure pulse to the lungs.

Determining the point in time of arrival, $t_{arr\_pulm}$, of the blood pressure pulse to the lungs of the ventilated subject based on a change in the measured respiratory pressure and/or the measured respiratory flow is advantageous in that $t_{arr\_pulm}$ can be determined from measurements obtained by conventional pressure and/or flow sensors of the breathing apparatus providing the mechanical ventilation of the patient.

In contrast to the FOT approach described in US 2016/0066801 where high frequency pressure oscillations are superimposed onto the respiratory pressure in order to determine $t_{arr\_pulm}$ from changes in airway impedance caused by changes in the geometry of the airways upon arrival of the blood pressure pulse to the lungs of the subject, the present disclosure hence suggests $t_{arr\_pulm}$ to be determined from a change in the respiratory pressure and/or the respiratory flow, which change is the result of a naturally occurring change in lung volume of the ventilated subject, caused by the arrival of the blood pressure pulse to the lungs of the subject. Thus, while FOT is an active technique in the meaning of requiring manipulation of the ongoing mechanical ventilation (through the application of the high frequency pressure oscillations onto the respiratory pressure), the proposed technique of determining tam pulm directly from changes in the measured respiratory pressure and/or flow is a passive technique requiring no adaption of the ongoing mechanical ventilation of the patient The time of arrival, $t_{arr\_pulm}$, of the blood pressure pulse may be determined directly from a change in the measured respiratory pressure and/or the measured respiratory flow. That $t_{arr\_pulm}$ is determined directly from the change in the measured respiratory pressure and/or the measured respiratory flow means that no other physical quantities are used in the determination of $t_{arr\_pulm}$, and that no specific relationship between pressure and flow has to be calculated and analysed to determine $t_{arr\_pulm}$. For instance, while the FOT based approach requires analysis of the frequency-dependent behaviour of Zrs, i.e. the complex relationship between applied pressure oscillations and resulting flow, the proposed approach allows $t_{arr\_pulm}$ to be determined directly from changes in either or both of a measured respiratory pressure or a measured respiratory flow. This has the effect of enabling quick, precise and computational-friendly monitoring of the hemodynamic parameters.

The arrival time, $t_{arr\_pulm}$, may be determined from a change in magnitude of the measured respiratory pressure and/or the measured respiratory flow. For example, $t_{arr\_pulm}$ may be determined as the point in time at which the measured respiratory pressure and/or the measured respiratory flow reaches a threshold value.

Alternatively, $t_{arr\_pulm}$ may be determined by analysing the curvature of a respiratory pressure curve and/or a respiratory flow curve, representing the change over time of the measured respiratory pressure and the measured respiratory flow, respectively. For example, $t_{arr\_pulm}$ may be determined based on a change in a first and/or second order derivative with respect to time of the respiratory pressure curve and/or the respiratory flow curve. This is advantageous in that the first and/or second order derivative of the respiratory pressure curve and/or the respiratory flow curve may be affected to a greater extent than the amplitudes of the respiratory pressure curve and the respiratory flow curve at the time of arrival of the blood pressure pulse at the lungs of the patient. Consequently, studying changes in the first and/or second order derivative may provide a more precise and/or robust estimation of $t_{arr\_pulm}$.

The method may further comprise a step of estimating a time window for the arrival of the blood pressure pulse to the lungs of the subject based on at least one parameter indicative of an approximate point in time of arrival of the blood pressure pulse to the lungs of the subject, and determining $t_{arr\_pulm}$ based on the respiratory pressure and/or respiratory flow measured during the estimated time window. This may prevent fluctuations in the measured respiratory pressure and/or respiratory flow not caused by the arrival of a blood pressure pulse to the lungs of the subject from being mistaken for pulmonary-flow induced cardiogenic oscillations, and so makes the method more robust.

The time window for the arrival of the blood pressure pulse to the lungs of the subject may be estimated from any parameter indicative of the approximate point in time of arrival of the blood pressure pulse to the lungs of the subject, including but not limited to the point in time, $t_{hb}$, of the heartbeat;

the point(s) in time of one or more previous heartbeats;

the point(s) in time of arrival at the lungs of the subject of one or more previous blood pressure pulses generated by the one or more previous heartbeats.

Consequently, the present disclosure suggests hemodynamic parameters related to the pulmonary circulatory system of the ventilated subject, such as PCO and PBF, to be determined from a point in time of a heartbeat, $t_{hb}$, and a point in time of arrival, $t_{arr\_pulm}$, of the blood pressure pulse to the lungs of the subject, both of which are determined based on changes in a measured respiratory pressure and/or a measured respiratory flow. This is advantageous in that no other quantities than respiratory pressure and/or respiratory flow and hence no other sensors than pressure and/or flow sensors normally existing in a ventilation system are required for the determination of the hemodynamic parameter. For instance, in contrast to the FOT approach, no phonocardiograph or ECG equipment is needed for determining the point in time of the heartbeat, and no loudspeaker or high frequency oscillator is required to determine the point in time of arrival of the blood pressure pulse to the lungs of the ventilated subject.

Another advantage of determining both $t_{arr\_pulm}$ and $t_{hb}$ from changes in the respiratory pressure and/or the respiratory flow is that the time delay between the point in time of a heartbeat and the point in time of detection of the heartbeat from the measured respiratory pressure and/or flow substantially corresponds to the time delay between the point in time of arrival of the blood pressure pulse at the lungs of the subject and the point in time of detection of arrival of the blood pressure pulse from the measured respiratory pressure and/or flow. Therefore, no time delay compensation is needed in the determination of $t_{arr\_pulm}$ and $t_{hb}$, which facilitates determination of the hemodynamic parameter and makes the determination more precise.

Changes in respiratory pressure and/or respiratory flow caused by heartbeats or the arrival of a blood pressure pulses to the lungs of the ventilated subject are normally referred to as cardiogenic oscillations. The phenomenon of cardiogenic oscillations is well-known in the art of mechanical ventilation and is normally regarded as an undesired artefact that distorts respiratory pressure and flow readings and adds noise to the pressure and flow curves normally presented to the operator of the breathing apparatus performing the mechanical ventilation. Thus, according to some aspects of the present disclosure, the time of the heartbeat, $t_{hb}$, is determined from heartbeat-induced cardiogenic oscillations in the measured respiratory pressure and/or flow, whereas the point in time of arrival of the blood pressure pulse to a point of arrival in the circulatory system of the ventilated subject is determined as a point in time of arrival, $t_{arr\_pulm}$, of the blood pressure pulse to the lungs of the subject, determined from pulmonary-flow induced cardiogenic oscillations.

When determining the and/or $t_{arr\_pulm}$ from changes in measured respiratory pressure and/or respiratory flow, $t_{hb}$ and/or $t_{arr\_pulm}$ is preferably determined for a heartbeat occurring during a final phase of inspiration or expiration when the respiratory flow is relatively low. This facilitates identification of cardiogenic oscillations in the respiratory pressure and flow, and thus improves the robustness of the proposed method.

This feature may be implemented through an additional step of confirming that the determined $t_{hb}$ and/or $t_{arr\_pulm}$ relate to a heartbeat occurring during a low flow period of respiration, such as a final phase of inspiration or expiration, and to determine the hemodynamic parameter from $t_{hb}$ and/or $t_{arr\_pulm}$ only if it can be confirmed that the heartbeat has occurred during a low flow period of respiration.

The method may further comprise the steps of determining a pulmonary pulse transit time, $PTT_{pulm}$, for the blood pressure pulse propagating along the pulmonary artery of the subject based on $t_{hb}$ and $t_{arr\_pulm}$, and determining the hemodynamic parameter based on the pulmonary $PTT_{pulm}$.

$PTT_{pulm}$ may be determined as the difference in time between $t_{hb}$ and $t_{arr\_pulm}$, which means that the $PTT_{pulm}$ may be determined as the difference in time between a first change in the measured respiratory pressure and/or flow, caused by the actual beat of the heart, and a second change in the measured respiratory pressure and/or flow, caused by a change in lung volume resulting from the arrival of a blood pressure pulse generated by said heartbeat to the lungs of the ventilated subject.

The hemodynamic parameter determined from $PTT_{pulm}$ may be the PBP or the PCO of the ventilated subject.

PBP may be determined from the relationship $$PBP = -\frac{2}{\propto} \cdot \ln PTT_{pulm} + \frac{\ln \frac{2r\rho L^2}{hE_0}}{\alpha}$$

where $\alpha$ is a constant, $PTT_{pulm}$ is the pulmonary PTT determined in accordance with the above mentioned principles, r is the inner radius of the pulmonary artery, $\rho$ is the blood density, L is the length of the pulmonary artery, h is the pulmonary artery wall thickness, and $E_0$ is the zero-pressure elastic modulus of the pulmonary artery wall.

PCO may be determined from the relationship $$PCO = K \times (\alpha \times PTT_{pulm} + \beta) \times HR$$

where $\alpha$ is a constant, K and $\beta$ are constants that are adapted to the ventilated subject (3), $PTT_{pulm}$ is the pulmonary PTT determined in accordance with the above mentioned principles, and HR is the heartrate of the ventilated subject.

If the hemodynamic parameter that is to be determined is a hemodynamic parameter relating to the systemic circulatory system of the subject, such as SBP or SCO, the point in time of arrival of the blood pressure pulse may be determined as a point in time of arrival ($t_{arr\_sys}$) of the blood pressure pulse to a point of arrival in the systemic circulatory system of the ventilated subject For example, $t_{arr\_sys}$ may be a point in time of arrival of the blood pressure pulse to a point of blood oxygenation measurement in a systemic artery of the ventilated subject. In this case, the method may comprise the steps of measuring a blood oxygenation at a point of blood oxygenation measurement in the systemic circulatory system of the subject, and determining $t_{arr\_sys}$ based on a change in the measured blood oxygenation.

The method may further comprise the steps of determining a systemic pulse transit time ($PTT_{sys}$) for the blood pressure pulse based on the and $t_{arr\_sys}$, and determining the hemodynamic parameter based on $PTT_{sys}$.

The hemodynamic parameter determined from $PTT_{sys}$ may be the SBP or the SCO of the ventilated subject.

SBP may be determined from the relationship $$SBP = -\frac{2}{\propto} \cdot \ln PTT_{sys} + \frac{\ln \frac{2r\rho L^2}{hE_0}}{\alpha}$$

where $\alpha$ is a constant, $PTT_{sys}$ is the systemic pulse transit time, r is the inner radius of the blood vessel, $\rho$ is the blood density, L is the length of the blood vessel, h is the vessel wall thickness, and $E_0$ is the zero-pressure elastic modulus of the vessel wall.

SCO may be determined from the relationship $$SCO = K \times (\alpha \times PTT_{sys} + \beta) \times HR$$

where $\alpha$ is a constant, K and $\beta$ are constants that are adapted to the ventilated subject (3), $PTT_{sys}$ is the systemic pulse transit time, and HR is the heartrate of the ventilated subject (3).

The hemodynamic parameter may also be the cardiac shunt of the ventilated subject, which cardiac shunt is determined based on a relationship between PCO and SCO, where any or both of PCO and SCO is determined in accordance with the above described principles. Such non-invasive determination of cardiac shunt during mechanical ventilation may, for instance, be used in the diagnosis of ventricular septal defect (VSD).

The method may further comprise a step of presenting the determined hemodynamic parameter to an operator of the breathing apparatus providing the mechanical ventilation of the subject, or to other medical personnel. For example, the determined hemodynamic parameter may be displayed on a display of a breathing apparatus carrying out the mechanical ventilation of the subject, or on a display of a patient monitor for monitoring the ventilated subject. The method may further comprise a step of generating an alarm signal in case the determined hemodynamic parameter falls outside a predefined range.

According to another aspect of the present disclosure there is provided a ventilation system comprising a computer configured to perform the above described method of non-invasive determination of a hemodynamic parameter of a mechanically ventilated subject based on a point in time, $t_{hb}$, of a heartbeat of the subject and an arrival point in time at which a blood pressure pulse caused by the heartbeat reaches a point of arrival in the circulatory system of the subject.

The computer is configured to obtain measurements of a respiratory pressure and/or a respiratory flow, and to determine $t_{hb}$ from a change in the measured respiratory pressure and/or the respiratory flow resulting from a physical impact of the heart on the lungs of the subject during the heartbeat. The computer may be the computer of a breathing apparatus carrying out the mechanical ventilation of the subject, such as a ventilator or an anaesthesia machine, or it may be a computer of a patient monitor for monitoring the ventilated subject. It may also be an external computer configured to receive respiratory pressure and/or flow measurements obtained by sensors of the ventilation system.

The ventilation system may comprise at least one pressure sensor and/or at least one flow sensor for obtaining the respiratory pressure and/or the respiratory flow measurements used by the computer in the determination of the hemodynamic parameter of the subject. The at least one pressure sensor and/or the at least one flow sensor may be internal sensors of the breathing apparatus or external sensors connected to the breathing apparatus, a patient monitor or an external computer for determining the hemodynamic parameter based on the measured respiratory pressure and/or flow.

The computer may be configured to determine the in accordance with any of the principles described above.

Likewise, the computer may be configured to determine the arrival point in time at which a blood pressure pulse caused by the heartbeat reaches the point of arrival in the circulatory system of the subject in accordance with any of the principles described above.

For example, the computer may be configured to determine the point in time of arrival of the blood pressure pulse as a point in time of arrival, $t_{arr\_pulm}$, of the blood pressure pulse to the lungs of the subject, which point in time of arrival is determined based on changes in the measured respiratory pressure and/or respiratory flow. The computer may then determine the hemodynamic parameter based on a pulmonary pulse transit time, $PTT_{pulm}$, calculated from $t_{hb}$ and $t_{arr\_pulm}$.

Alternatively, the computer may be configured to determine the point in time of arrival of the blood pressure pulse as a point in time of arrival, $t_{arr\_sys}$, of the blood pressure pulse to a point of arrival in the systemic circulatory system of the subject, which point in time of arrival may be determined based on e.g. a change in blood oxygenation, measured at the point of arrival. The computer may then determine the hemodynamic parameter based on a systemic pulse transit time, $PTT_{sys}$, calculated from $t_{hb}$ and $t_{arr\_sys}$.

The logic required to enable the ventilation system to carry out the steps of the above-described method is typically implemented by means of software. Thus, according to yet another aspect of the present disclosure there is provided a computer program for non-invasive determination of a hemodynamic parameter of a mechanically ventilated subject based on a point in time, $t_{hb}$, of a heartbeat of the subject and an arrival point in time at which a blood pressure pulse caused by the heartbeat reaches a point of arrival in the circulatory system of the subject. The computer program comprises computer-readable code segments which, when executed by a computer of the ventilation system, causes the computer to:

obtain measurements of a respiratory pressure and/or a respiratory flow, and determine the point in time, $t_{hb}$, of the heartbeat from a change in the measured respiratory pressure and/or the respiratory flow resulting from a physical impact of the heart on the lungs of the subject during the heartbeat.

The computer program may, for instance, be stored in a non-volatile memory of the apparatus.

Installation of the computer program on existing apparatuses configured to obtain respiratory gas pressure and/or respiratory gas flow measurements, such as conventional breathing apparatuses and patient monitors equipped with sensors for measuring any or both of a respiratory pressure and a respiratory flow, may allow existing apparatuses to carry out the method of the present disclosure without any hardware modification.

More advantageous aspects of the proposed method, apparatus and computer program will be described in the detailed description of embodiments following hereinafter.

BRIEF DESCRIPTION OF THE DRAWINGS

The present invention will become more fully understood from the detailed description provided hereinafter and the accompanying drawings which are given by way of illustration only. In the different drawings, same reference numerals correspond to the same element.

DETAILED DESCRIPTION

Figure 1:
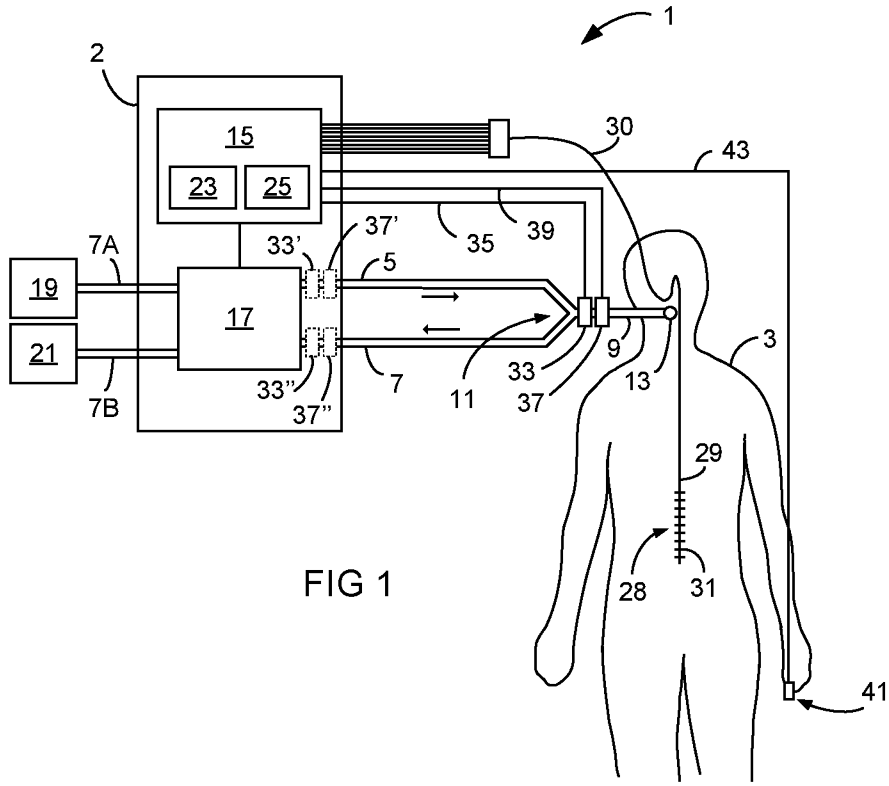
FIG. 1 illustrates a ventilation system comprising a breathing apparatus capable of non-invasively determining a hemodynamic parameter of a ventilated patient.

FIG. 1 illustrates an exemplary embodiment of a ventilation system 1 comprising a breathing apparatus 2 configured to determine a hemodynamic parameter of a mechanically ventilated subject 3 (hereinafter referred to as the patient) according to the principles disclosed herein. The breathing apparatus 2 may be any type of apparatus capable of providing ventilatory assist to the subject 3 through the supply of pressurised breathing gas to the airways of the subject. Ventilators and anaesthesia machines are non-limiting examples of such breathing apparatuses.

The breathing apparatus 2 is connected to the patient 3 via a patient circuit comprising an inspiratory line 5 for supplying breathing gas to the patient 3, and an expiratory line 7 for conveying expiration gas away from the patient 3. The inspiratory line 5 and the expiratory line 7 are connected to a common line 9, via a so called Y-piece 11, which common line is connected to the patient 3 via a patient connector 13, such as a facemask or an endotracheal tube.

The breathing apparatus 2 comprises a control unit or control computer 15 for controlling the ventilation of the patient 3 based on pre-set parameters and/or measurements obtained by various sensors of the breathing apparatus. The control computer 15 controls the ventilation of the patient 3 by controlling a pneumatic unit 17 of the breathing apparatus 2, which pneumatic unit 17 is connected on one hand to one or more gas sources 19, 21 and on the other hand to the inspiratory line 5 for regulating a flow and/or pressure of breathing gas delivered to the patient 3. The pneumatic unit 17 may comprise various gas mixing and regulating means well known in the art of ventilation, such as gas mixing chambers, controllable gas mixing valves, turbines, controllable inspiration and/or expiration valves, etc. The pneumatic unit 17 is connected to the inspiratory line 5 of the patient circuit via an internal inspiratory flow channel of the breathing apparatus 2, and to the expiratory line 7 of the patient circuit via an internal expiratory flow channel of the breathing apparatus. The gas flow path of the ventilation system 1 that is arranged in fluid communication with the airways of the patient 3 during operation of the breathing apparatus may herein be referred to as the breathing circuit of the ventilation system. The breathing circuit includes at least the patient circuit and the inspiratory and expiratory flow channels of the breathing apparatus 2.

The control computer 15 comprises a processor or processing unit 23, such as a microprocessor, and a non-volatile memory hardware device 25 storing one or more computer programs for controlling the operation of the breathing apparatus 2 and for determining the hemodynamic parameter of the patient 3 in accordance with the principles described herein. Unless stated otherwise, actions and method steps described hereinafter are performed by, or caused by, the control computer 15 of the breathing apparatus 2 upon execution by the processing unit 23 of different code segments of a computer program stored in the memory 25.

The computer program may comprise code segments which, when executed, causes the control computer 15 to determine a hemodynamic parameter of the ventilated patient 3 based on a point in time ($t_{hb}$) of a heartbeat of the patient and an arrival point in time ($t_{arr\_pulm}$) at which a blood pressure pulse caused by the heartbeat reaches the lungs of the patient. The code segments may cause the control computer to obtain measurements of a respiratory pressure and/or a respiratory flow, and to determine $t_{arr\_pulm}$ from a change in the measured respiratory pressure and/or the respiratory flow resulting from a change in lung volume caused by the arrival of the blood pressure pulse to the lungs of the patient.

As briefly discussed above, a change in a respiratory pressure or flow caused by the arrival of a blood pressure pulse to the lungs of the ventilated patient is normally referred to as a cardiogenic oscillation. There are basically two different types of cardiogenic oscillations; pulmonary-flow induced cardiogenic oscillations and heartbeat-induced cardiogenic oscillations. A pulmonary-flow induced cardiogenic oscillation is a cardiogenic oscillation resulting from a change in lung volume caused by the arrival of a blood pressure pulse generated by a heartbeat to the lungs of the subject. A heartbeat-induced cardiogenic oscillation is a cardiogenic oscillation resulting from the propagation in lung tissue of a pressure pulse generated by the physical impact of the heart on the lung tissue during a heartbeat.

Consequently, the computer program can be said to cause the control computer 15 to determine $t_{arr\_pulm}$ based on a pulmonary-flow induced cardiogenic oscillation in a monitored respiratory pressure and/or a respiratory flow.

The ventilation system 1 comprises at least one of a flow sensor 33 for measuring a respiratory flow of gas and a pressure sensor 37 for measuring a respiratory gas pressure. In the exemplary embodiment illustrated in FIG. 1, the flow sensor 33 is located in or close to the Y-piece 11 and configured to measure both an inspiratory flow of breathing gas delivered towards the patient 3 during inspiration, and an expiratory flow of gas exhaled by the patient 3 during expiration. Likewise, the pressure sensor 37 is located in or close to the Y-piece 11 and configured to measure a proximate patient pressure, substantially corresponding to and often referred to as an airway pressure of the patient 3, during both inspiration and expiration. The measurement signals obtained by the flow sensor 33 and the pressure sensor 37 are transmitted to the control computer 15 via a respective signalling line 35, 39, whereby the measurement signals are used by the control computer in the determination of the hemodynamic parameter of the patient 3. The flow and/or pressure measurements signals received by the control computer 15 from the flow and/or pressure sensors 33, 37 may further be used by the control computer 15 in automatic feedback control of the operation of the breathing apparatus 2, in accordance with principles well known in the art of ventilation.

Alternatively or in addition to the flow sensor 33 and/or the pressure sensor 37 in the Y-piece 11 of the patient circuit, the breathing apparatus 2 may comprise one or more internal flow sensors for measuring respiratory gas flow, and/or one or more internal pressure sensors for measuring respiratory gas pressure. For example, the breathing apparatus 2 may comprise a flow sensor 33' for measuring a flow of breathing gas in the inspiratory flow channel of the breathing apparatus, and/or a pressure sensor 37' for measuring a gas pressure in the inspiratory flow channel of the breathing apparatus. Alternatively, or in addition, the breathing apparatus 2 may comprise a flow sensor 33" for measuring a flow of expiration gas in the expiratory flow channel of the breathing apparatus, and/or a pressure sensor 37" for measuring a gas pressure in the expiratory flow channel of the breathing apparatus.

The respiratory pressure and/or flow measurements used by the control computer 15 to determine the hemodynamic parameter may be obtained by any of, or any combination of, the exemplary flow and pressure sensors 33-33", 37-37" illustrated in FIG. 1, or by pressure and/or flow sensors for measuring respiratory flow and/or respiratory pressure disposed elsewhere in the breathing circuit of the ventilation system 1.

In another example, the respiratory pressure and/or flow measurements used by the control computer 15 to determine the hemodynamic parameter may be obtained by a pressure and/or a flow sensor inserted into the trachea of the patient 3. Such a pressure and/or flow sensor may, for instance, be mounted onto a tracheal tube for intubation of the patient 3 during ventilation. As will be appreciated from the description following hereinafter, it may be advantageous to use pressure and/or flow sensors located proximate to the airway opening of the patient 3, e.g. sensors located in the Y-piece 11 or even in the trachea of the patient 3, so as to minimize the distance between the lungs of the patient 3 and the point of pressure and/or flow measurement.

The control computer 15 may be configured to derive a respiratory pressure curve and/or a respiratory flow curve from the respiratory pressure and/or flow measurements, and to present the respiratory pressure curve and/or the respiratory flow on a display (not shown) of the breathing apparatus 2. Changes in measured respiratory pressure and/or respiratory flow may be identified and quantified by the control computer 15 by analysing changes in the amplitude and/or the curvature of the respiratory pressure curve and/or the respiratory flow curve. Hereinafter, the term “respiratory curve” may sometimes be used as a general term for any of a respiratory pressure curve or a respiratory flow curve representing the measured respiratory pressure and the measured respiratory flow, respectively.

The ventilation system 1 may further comprise an ECG sensor arrangement 28 configured to register ECG signals indicative of the electrical activity of the heart of the ventilated patient 3. The ECG related signals recorded by the ECG sensor arrangement 29 are transmitted to the control computer 15 of the breathing apparatus 2 via a signalling line 30. In some embodiments, the ECG signals may then be used by the control computer 15 in the determination of the hemodynamic parameter of the patient 3, as further described below.

In the illustrated embodiment, the breathing apparatus 2 is a NAVA-enabled ventilator comprising a bioelectric sensor arrangement coupled to the control computer 15 of the breathing apparatus 1. The bioelectric sensor arrangement comprises an electromyogram (EMG) detector for recording the diaphragm EMG of the patient 3. The EMG detector comprises an oesophageal catheter 29 carrying an array of electrodes 31 for capturing EMG signals from the diaphragm of the patient 3. The electrodes 31 produce a number of subsignals that are processed by the control computer 15 to calculate a signal, the Edi signal, representing the electrical activity of the diaphragm (EAdi). Since the EMG signals captured by the sensor are used to calculate an Edi signal, the oesophageal catheter 29 is often referred to as an Edi catheter within the field of ventilation.

Besides the Edi signal, the control computer 15 is configured to derive an ECG signal from the recorded diaphragm EMG, which ECG signal is indicative of the electrical activity of the patient's heart. How to extract an ECG signal from the diaphragm EMG captured by the electrodes of the oesophageal catheter 29 is well known in the art and disclosed in e.g. U.S. Pat. No. 8,527,036. Consequently, in this exemplary embodiment, the ECG sensor arrangement 28 is a bioelectric sensor arrangement constituting a combined Edi and ECG sensor arrangement.

In other embodiments, other types of sensors may be used to capture the ECG signal of the ventilated patient 3. For example, conventional ECG surface electrodes for placement on the skin of the ventilated patient 3 may be used.

The ventilation system 1 further comprises a blood oxygen sensor 41, such as a pulse oximeter, for obtaining measurements of the oxygen content or concentration in the ventilated patient's blood. The blood oxygen sensor 41 may be attached to a body part of the patient 3, such as a fingertip, an earlobe or a foot, in order to obtain blood oxygenation data relating to the oxygenation of blood in that specific body part. The blood oxygenation data may, for instance, comprise data on peripheral oxygen saturation (SpO2). The blood oxygenation data may be transmitted to the control computer 15 of the breathing apparatus 2 via a signalling line 43, whereby the control computer 15 may use the received blood oxygenation data in the determination of the hemodynamic parameter of the patient 3, as further described below.

Figure 2:
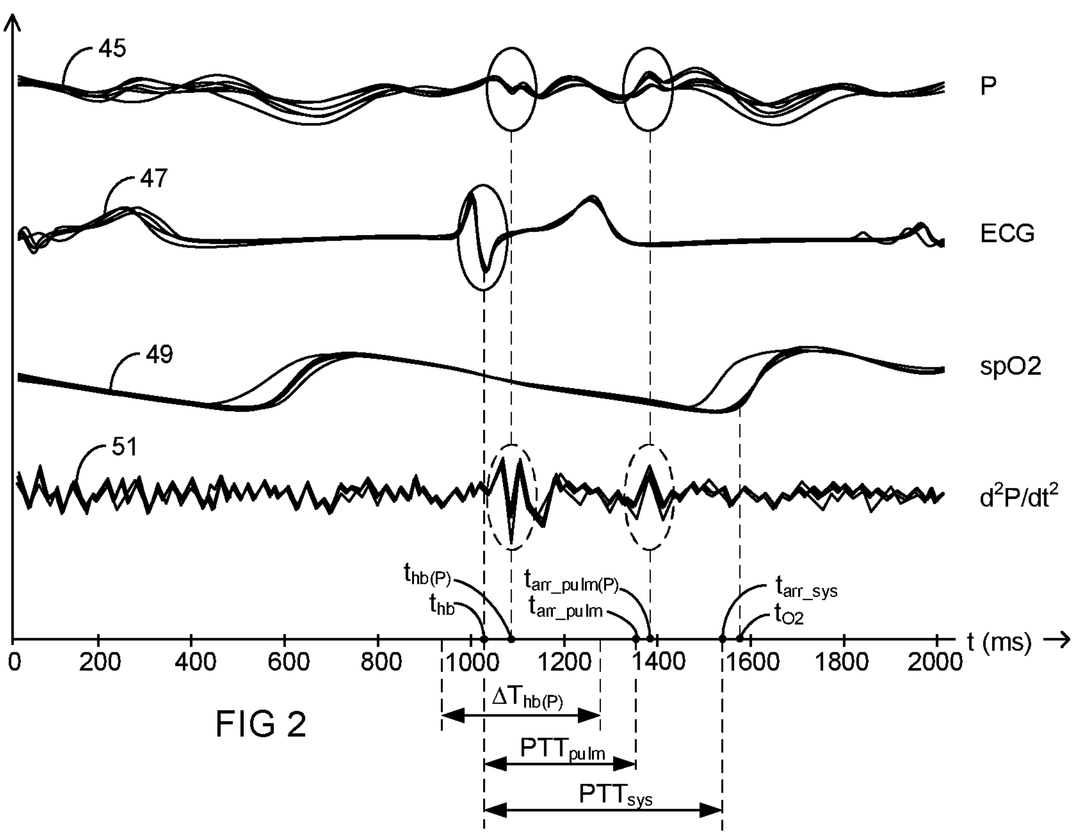
FIG. 2 illustrates curves of measured quantities that may be used in the determination of the hemodynamic parameter.

FIG. 2 illustrates a respiratory pressure curve 45, an ECG 47, an SpO2 curve 49 and a curve 51 representing the second order time derivatives (P") of the respiratory pressure curve 45. Only to illustrate variations in the respective quantity between different heartbeats, multiple curves obtained during different heartbeats are shown for the respective quantity.

With simultaneous reference now made to FIG. 1, the respiratory pressure curve 45, the ECG 47, the SpO2 curve 49 and the P" curve 51 may be derived by the control computer 15 of the breathing apparatus 2 from measurements obtained by the sensors of the ventilation system 1 during a time period including a heartbeat of the patient 3. The respiratory pressure curve 45 is an exemplary respiratory curve that may be derived by the control computer 15 based on measurements received from any of, or any combination of, the pressure sensors 37-37". For example, the respiratory pressure curve 45 may represent an airway pressure (Paw) of the patient 3. The ECG 47 may be derived by the control computer 15 based on measurements obtained by the ECG sensor arrangement 28. The SpO2 curve may be derived by the control computer 15 based on measurements obtained by the blood oxygen sensor 41. The P" curve 51 may be derived by the control computer from the respiratory pressure curve 45.

When the heart of the patient 3 beats, a pulse propagates through the lung tissue of the patient and further on into the breathing circuit of the ventilation system 1 via gas in the lungs and the airways of the patient. This gas pulse, hereinafter referred to as the heartbeat-induced gas pulse, may be detected by studying changes in magnitude or curvature of a respiratory curve derived from sensor measurements in the breathing circuit, such as the respiratory pressure curve 45 in FIG. 2. As mentioned above, such changes in the respiratory curve are normally referred to as heartbeat-induced cardiogenic oscillations.

The arrival of the heartbeat-induced gas pulse to the point of pressure measurement in the breathing circuit causes a characteristic change in the curvature of the respiratory pressure curve 45. In FIG. 2, the point in time for this characteristic change in curvature of the respiratory pressure curve 45 is denoted $t_{hb(P)}$. The control computer 15 may be configured to detect this change and use it to calculate an actual point in time of the heartbeat, $t_{hb}$. The actual point in time of the heartbeat, $t_{hb}$, may be determined by the control computer 15 as the point in time $t_{hb(P)}$ at which the characteristic change in curvature of the respiratory pressure curve 45 occurs, minus a known time delay. The time delay depends, for instance, on pulse propagation velocity and distance in tissue, pulse propagation velocity and distance in gas, and a measurement delay of the sensor system. In other embodiments the control computer 15 may be configured to ignore the time delay and set the to equal $t_{hb(P)}$.

Furthermore, when the heart of the patient 3 beats, a flow of deoxygenated blood is pumped from the heart towards the lungs of the patient. This flow of blood constitutes a blood pressure pulse that propagates from the heart towards the lungs of the patient, via the pulmonary arteries. Upon arrival of the blood pressure pulse at the lungs of the patient, the expansion of the pulmonary capillaries causes the blood pressure pulse to propagate into the gas of the alveoli. The gas pulse thus created, hereinafter referred to as the blood-pulse induced gas pulse, may also be detected by studying changes in magnitude or curvature of a respiratory curve derived from sensor measurements in the breathing circuit, such as the respiratory pressure curve 45 in FIG. 2. As mentioned above, such changes in the respiratory curve is normally referred to as pulmonary-flow induced cardiogenic oscillations.

The arrival of the blood-pulse induced gas pulse to the point of pressure measurement in the breathing circuit causes a characteristic change in the curvature of the respiratory pressure curve 45. In FIG. 2, the point in time for this characteristic change in curvature of the respiratory pressure curve 45 is denoted $t_{arr\_pulm(P)}$. The control computer 15 may be configured to detect this change and to use it to determine a point in time of arrival, $t_{arr\_pulm}$, of the blood pressure pulse to the lungs of the patient 3. In some embodiments, the small time delay between the arrival of the blood pressure pulse to the lungs of the patient 3 and the detection of the blood-pulse induced gas pulse in the breathing circuit may be ignored, whereby $t_{arr\_pulm}$ can be assumed to correspond to $t_{arr\_pulm(P)}$. In other embodiments, the time delay may be taken into account, whereby $t_{arr\_pulm}$ may be calculated by the control computer 15 as $t_{arr\_pulm(P)}$ minus a certain time delay, which time delay depends on pulse propagation velocity and distance, as well as a measurement delay of the sensor system.

To maximize the chance of detection of the heartbeat-induced gas pulse and/or the blood-pulse induced gas pulse from the respiratory curve, such as the respiratory pressure curve 45, the control computer 15 may be configured to perform the determination of the pulmonary blood pressure of the patient 3 based on a heartbeat that occurs during a low flow period of respiration, i.e. a period of low respiratory flow in the breathing circuit, and preferably during a period of substantially constant flow. The low flow period may, for instance, be a final phase of inspiration or a final phase of expiration. Alternatively, the control computer 15 may be configured to perform the determination during a period of essentially zero flow in the breathing circuit, e.g. during an inspiratory pause, an expiratory pause or even an occlusion manoeuvre. In the following it will be assumed that determination of the hemodynamic parameter is made based on a heartbeat that occurs during a final phase of inspiration. At the end of inspiration, the flow of respiratory gases in the breathing circuit is low and the lung pressure of the patient 2 is substantially constant, thereby facilitating detection of the heartbeat-induced gas pulse and the blood-pulse induced gas pulse from a respiratory pressure or flow curve derived by the control computer 15. To this end, the control computer 15 may be configured to analyse the respiratory curve only within an end-inspiratory time window in order to identify the point in time of the heartbeat, $t_{hb}$, and/or the point in time of arrival of the blood pressure pulse to the lungs of the patient, $t_{arr\_pulm}$.

The control computer 15 may be configured to determine any one or both of the point in time of the heartbeat, $t_{hb}$, and the point in time of arrival of the blood pressure pulse to the lungs of the patient 3, $t_{arr\_pulm}$, by analysing the magnitude of the respiratory curve. For example $t_{hb}$ and/or $t_{arr\_pulm}$ may be determined by the control computer 15 based on the crossing of the respiratory curve of one or more predetermined threshold values. However, measurement noise and natural pressure and flow fluctuations in the breathing circuit may, in this instance, cause "false triggering" and thus render detection of the pulses difficult. Therefore, to improve the robustness of the method, the control computer 15 may also be configured to analyse the curvature of the respiratory curve, instead or in addition to the magnitude thereof.

For example, the control computer 15 may be configured to study a first and/or second order time derivative of the respiratory curve, and preferably a second order time derivative of the respiratory curve. As illustrated by the P" curve 51 in FIG. 2, the characteristic changes in the respiratory pressure curve 45 caused by the arrival of the heartbeat- and blood-pulse induced gas pulses to the sensor becomes even more distinct when studying the second order derivative, thereby facilitating determination of $t_{hb}$ and $t_{arr\_pulm}$. As discussed above, to further facilitate determination of $t_{hb}$ and/or $t_{arr\_pulm}$, the control computer 15 may be configured to analyse the P" curve only within a time window with low respiratory flow, such as an end-inspiratory or end-expiratory time window.

In some embodiments, the control computer 15 may be configured to use blood oxygenation data relating to the oxygenation of blood in a body part of the ventilated patient 3 to further facilitate detection of the heartbeat-induced gas pulse and the determination of $t_{hb}$. According to one example, the control computer 15 may use the SpO2 curve 49 registered by the blood oxygen sensor 41, illustrated in FIG. 2. By analysing the obtained blood oxygenation data, the control computer 15 can determine an approximate time for the heartbeat based on a change (increase) in measured blood oxygenation. By first determining an approximate time for the heartbeat, detection of the heartbeat-induced gas pulse in the respiratory curve is facilitated. The approximate time of the heartbeat may be determined by the control computer 15 based on the time of detection of the change in oxygenation (denoted $t_{O2}$ in FIG. 2) and an estimated systemic PTT for a systemic blood pressure pulse propagating from the patient's heart to the point of blood oxygen measurement. The systemic PTT may be estimated based on a measured or assumed distance between the patient's heart and the point of measurement (typically estimated as 0.5× patient length for fingertip measurements), a measured or assumed systemic blood pressure of the patient, and an assumed compliance of the systemic arteries of the patient. Typically, the systemic PTT is estimated by the control computer 15 based on body measures of the ventilated patient 3 alone. For example, the control computer 15 may be configured to estimate the systemic PTT based on patient data that are input to the breathing apparatus 2 by an operator, e.g. patient data relating to the height of the ventilated patient 3.

The above described functionality may, for example, be implemented by having the control computer 15 determine a time window for the heartbeat, denoted $\Delta T_{hb(P)}$ in FIG. 2, within which the heartbeat-induced gas pulse can be assumed to cause a detectable change in the respiratory curve. The boundaries of the time window $\Delta T_{hb(P)}$ may be set by the control computer 15 based on an uncertainty in the determination of the approximate time of the heartbeat. The control computer 15 may then be configured to analyse the magnitude and/or curvature of the respiratory curve only within the determined time window $\Delta T_{hb(P)}$ for the heartbeat.

In other embodiments, the control computer 15 may use data other than blood oxygenation data in order to estimate an approximate time for the heartbeat. For instance, the control computer 15 may be configured to estimate a heart rate of the ventilated patient 3, and use the estimated heart rate to estimate an approximate time for the heartbeat. For example, the estimated heart rate may be used together with a determined point in time for at least one preceding heartbeat in order to calculate an approximate time for the heartbeat. The heart rate of the patient 3 may be estimated by the control computer 15 based on a plurality of previously determined points in time for a heartbeat, determined from a respiratory curve in accordance with the above described principles. Furthermore, the control computer 15 may utilize knowledge related to the ongoing respiratory treatment of the patient 3 in order to more accurately estimate an approximate time for the heartbeat. The heart rate and the timing of heartbeats of a subject are highly affected by the respiratory rate and the timing of respiration of the subject. Therefore, the control computer 15 may be configured to use sensor data indicative of the respiratory phases of the patient 3 to further improve estimation of the approximate time for the heartbeat. Such sensor data may relate to a respiratory pressure, a respiratory flow, and/or a bioelectric signal indicative of breathing efforts by the patient 3, such as an Edi signal. In accordance with the above described example, the control computer 15 may, after having estimated the approximate time for the heartbeat, define a time window for the heartbeat in which the respiratory curve is analysed in order to determine a more exact time for the heartbeat.

Furthermore, the control computer 15 may be configured to calculate an approximate time for the heartbeat retroactively based on the determined point in time, $t_{arr\_pulm}$, of arrival of the blood pressure pulse to the lungs of the patient 3. There may be circumstances in which the heartbeat-induced gas pulse is weak and difficult to identify in the respiratory curve, whereas the blood-pulse induced gas pulse is strong enough to be detected. In such situations, the time of detection of the blood-pulse induced gas pulse may give valuable information on the approximate time of the heartbeat. Once the arrival time, $t_{arr\_pulm}$, has been determined, the control computer 15 may calculate an approximate time of the heartbeat based on an estimated pulmonary PTT for propagation of the blood pressure pulse from the heart to the lungs of the patient 3. The estimated pulmonary PTT may be estimated by the control computer 15 based on patient data that are input to the breathing apparatus 2 by an operator, or it may be estimated based on points in time of one or more previous heartbeats and points in time of arrival of one or more previous blood pressure pulses at the lungs of the patient 3. In accordance with the above described examples, the control computer 15 may then use the approximate time of the heartbeat to define a time window in which the respiratory curve is further analysed to identify the actual point in time of the heartbeat, or rather the point in time $t_{hb}$ (P) from which the actual point in time $t_{hb}$ of the heartbeat may be determined.

In other circumstances, the heartbeat-induced gas pulse may be detected using one or more of the above described techniques, whereas the blood-pulse induced gas pulse is more difficult to detect. In such situations, the control computer 15 may be configured to use the in the determination of $t_{arr\_pulm}$. For instance, the control computer 15 may be configured to calculate an approximate time of arrival of the blood pressure pulse to the lungs of the patient 3 based on the determined $t_{hb}$ and the estimated pulmonary PTT. The control computer 15 may then determine a time window for the arrival of the blood pressure pulse to the lungs of the patient 3 based on the calculated approximate time of arrival, and analyse the respiratory curve within the determined time window to facilitate identification of the point in time $t_{arr\_pulm}$ (P) from which the actual point in time of arrival of the blood pressure pulse, $t_{arr\_pulm}$, can be determined.

Above, it has been described how the control computer 15 may determine both the point in time of the heartbeat, $t_{hb}$, and the point in time of arrival of the blood pressure pulse to the lungs of the patient 3, $t_{arr\_pulm}$, from a respiratory curve derived from respiratory pressure and/or flow measurements in the breathing circuit. However, in scenarios where an ECG of the patient 3 is available, such as the scenario illustrated in the drawings, the control computer 15 may be configured to use the ECG signal to determine the point in time of the heartbeat, $t_{hb}$. For example, the control computer 15 may be configured to analyse the ECG and to determine the point in time of the heartbeat, $t_{hb}$, as the location of the R wave in the ECG QRS complex.

Furthermore, the steps involved in determination of the point in time of the heartbeat, $t_{hb}$, and the point in time of arrival of the blood pressure pulse to the lungs of the patient, $t_{arr\_pulm}$, have been described above with reference to the respiratory pressure curve 45 in FIG. 2. It should be noted, however, that the same or similar steps may be taken in order to determine the points in time of the heartbeat and arrival of the blood pressure pulse to the lungs of the patient from a respiratory flow curve obtained from respiratory gas flow measurements. In a breathing apparatus having zero breathing circuit resistance and ideal control of applied airway pressure, the measured pressure (also used for controlling the supply of breathing gas to the patient in a pressure controlled mode of ventilation) would typically be fixed during a main part of inspiration and a final phase of expiration, and any pressure fluctuations would be compensated for immediately. For such an ideal ventilator, during these periods of respiration, there would not be any pressure changes (and hence no detectable heartbeat or blood-pulse induced pressure changes) and changes in flow would be the only indicator of the heartbeat and the arrival of the blood pressure pulse to the lungs of the patient. For a typical breathing apparatus with non-zero patient circuit resistance and non-ideal control of applied airway pressure, however, heartbeat and blood-pulse induced pressure changes may be more easily detectable than heartbeat and blood-pulse induced flow changes. Therefore, depending on the characteristics of the breathing apparatus, it may be advantageous to use either a respiratory pressure curve or a respiratory flow curve in the determination of the points in time of the heartbeat and the arrival of the blood pressure pulse to the lungs of the patient. Of course, although not disclosed in any detail, it is possible to obtain and use both respiratory pressure and flow measurements in the determination of the and $t_{arr\_pulm}$. For example, the control computer 15 may be configured to obtain both a respiratory pressure curve and a respiratory flow curve, and to compare the curves with each other in order to increase robustness and/or improve accuracy in the determination of the point in time of the heartbeat and/or the point in time of arrival of the blood pressure pulse to the lungs of the patient.

Once the control computer 15 has determined the point in time of the heartbeat, $t_{hb}$, and the point in time of arrival of the blood pressure pulse to the lungs of the patient 3, $t_{arr\_pulm}$, it may calculate a pulmonary pulse transit time, $PTT_{pulm}$, for the propagation of the blood pressure pulse from the heart to the lungs of the patient, based on the determined $t_{hb}$ and $t_{arr\_pulm}$. The thus determined $PTT_{pulm}$ is hence an actual pulmonary PTT representing the transit time for the blood pressure pulse propagating from the heart to the lungs of the patient, along the pulmonary arteries, as a result of the heartbeat. $PTT_{pulm}$ may be determined by the control computer as the time elapsed between the heartbeat and the arrival of the blood pressure pulse at the lungs of the patient, i.e. as the difference between the and $t_{arr\_pulm}$. The thus determined $PTT_{pulm}$ may then be used by the control computer 15 to calculate different hemodynamic parameters relating to the pulmonary circulatory system of the patient, e.g. in accordance with the principles described hereinafter.

Determination of Pulmonary Blood Pressure (PBP)

The control computer 15 may calculate a pulmonary pulse wave velocity, PWV, of the blood pressure pulse based on $PTT_{pulm}$ and an assumed distance of pulse propagation between the heart and the lungs. The assumed distance of pulse propagation may, for instance, be determined by the control computer 15 based on patient data that are input to the breathing apparatus 2 by an operator, e.g. patient data relating to the height of the ventilated patient 3.

As well known in the art, the PWV of a blood pressure pulse may be expressed as a function of a volumetric elastance of the blood vessel in which the pulse propagates. When the blood pressure rises, the volumetric elastance of the vessel increases, the wall of the vessel becomes hard, and the PWV increases. Therefore, once the pulmonary PWV of the blood pressure pulse has been determined using the principles of the present disclosure, the control computer 15 may use the PWV to determine the PBP of the ventilated patient 3 using known principles of pulse propagation-based blood pressure determination. PBP is proportional to the PWV of the blood pressure pulse in the pulmonary arteries, and the constant of proportionality depends on the elastance of the pulmonary arteries of the patient. The elastance of the pulmonary arteries and hence the constant of proportionality between the determined pulmonary PWV and the PBP of the patient 3 may be set by the control computer 15 based on patient data that are input to the breathing apparatus 2 by an operator, e.g. patient data relating to the age of the ventilated patient. In other embodiments, the constant of proportionality may be determined by the breathing apparatus 2 based on data obtained during a calibration procedure involving systemic blood pressure measurements, e.g. based on data resulting from conventional blood pressure cuff measurements. Such data may be obtained automatically by the breathing apparatus 2 or be manually input to the breathing apparatus 2 by an operator.

In an exemplary embodiment, the PBP of the patient 3 may be calculated by the control computer 15 from $PTT_{pulm}$ based on the relationship $$PBP = -\frac{2}{\alpha} \cdot \ln PTT_{pulm} + \frac{\ln \frac{2r\rho L^2}{hE_0}}{\alpha}, \quad \text{(Eq. 1)}$$

where PBP is the pulmonary blood pressure, a is a constant, $PTT_{pulm}$ is the pulmonary pulse transit time determined in accordance with the above described principles, r is the inner radius of the blood vessel (i.e. the pulmonary artery), ρ is the blood density, L is the vessel length, h is the vessel wall thickness, and $E_0$ is the zero-pressure elastic modulus of the vessel wall.

Thus, by determining at least the point in time of arrival, $t_{arr\_pulm}$, of the blood pressure pulse to the lungs of the ventilated patient 3 from cardiogenic oscillations in a measured respiratory pressure and/or flow, the principles of the present disclosure allows a pulmonary PTT to be determined and used in a manner similar to the manner in which the systemic PTT is used in the above described technique for cuff-free blood pressure estimation according to prior art, thereby enabling non-invasive determination and monitoring of the PBP of the ventilated patient 3.

It should be noted that Equation 1 does not take variations in external pressure acting on the blood vessel into account. However, the external pressure of the pulmonary artery may vary quite significantly due to the expansion and contraction of lung tissue during respiration. The external pressure acting on the pulmonary artery is dependent on the current lung pressure of the ventilated patient 3 and, therefore, the control computer 15 may advantageously be configured to take the current lung pressure of the ventilated patient into account in the determination of PBP. Variations in external pressure on the pulmonary artery may be regarded as a change in elastance of the pulmonary artery. To account for the variations in lung pressure, the control computer 15 may therefore be configured to determine the elastance of the pulmonary artery as a function of lung pressure. Consequently, according to some embodiments, the constant zero-pressure elastic modulus $E_0$ in equation 1 may be exchanged for a variable and lung-pressure dependent elastance, $E(P_{lung})$, of the pulmonary artery. The lung pressure of the ventilated patient may be approximated by, or calculated from, the pressure measured by the pressure sensor 37 of the breathing apparatus, which pressure substantially corresponds to the airway pressure of the patient 3.

From the above, it should be appreciated that the method for non-invasive determination of a hemodynamic parameter as described herein may be a method for non-invasive determination of a PBP of a mechanically ventilated subject based on a point in time, $t_{hb}$, of a heartbeat of the subject and an arrival point in time, $t_{arr\_pulm}$, at which a blood pressure pulse caused by the heartbeat reaches the lungs of the subject. The method may comprise the steps of measuring a respiratory pressure and/or a respiratory flow, and determining $t_{arr\_pulm}$ from a change in the measured respiratory pressure and/or the respiratory flow resulting from a change in lung volume caused by the arrival of the blood pressure pulse to the lungs of the subject.

Determination of Pulmonary Cardiac Output (PCO)

It has been confirmed by clinical experiments that there is an inverse correlation between PTT and stroke volume (SV), even at varying vascular resistance. Therefore, the above described method for non-invasive determination of pulmonary PTT enables the control computer 15 to determine the pulmonary cardiac output of the ventilated patient 3 based on the determined pulmonary PTT and a heartrate of the patient. For example, using the principles of the esCCO approach, PCO may be determined by the control computer 15 from the relationship $$PCO = K \times (\alpha \times PTT_{pulm} + \beta) \times HR \quad \text{(Eq.2)}$$

where α is a constant, $PTT_{pulm}$ is the pulmonary pulse transit time determined in accordance with the above described principles, K and β are constants that are adapted to the ventilated patient 3, and HR is the heartrate of the patient.

Thus, by determining at least the point in time of arrival, $t_{arr\_pulm}$, of the blood pressure pulse to the lungs of the ventilated patient 3 from cardiogenic oscillations in a measured respiratory pressure and/or flow, the principles of the present disclosure allows a pulmonary PTT to be determined and used in a manner similar to the manner in which the systemic PTT is used in the esCCO approach, thereby enabling non-invasive determination and monitoring of the PCO of the ventilated patient 3.

From the above, it should be appreciated that the method for non-invasive determination of a hemodynamic parameter as described herein may be a method for non-invasive determination of PCO of a mechanically ventilated subject based on a point in time, $t_{hb}$, of a heartbeat of the subject and an arrival point in time, $t_{arr\_pulm}$, at which a blood pressure pulse caused by the heartbeat reaches the lungs of the subject. The method may comprise the steps of measuring a respiratory pressure and/or a respiratory flow, and determining $t_{arr\_pulm}$ from a change in the measured respiratory pressure and/or the respiratory flow resulting from a change in lung volume caused by the arrival of the blood pressure pulse to the lungs of the subject.

Figure 3A:
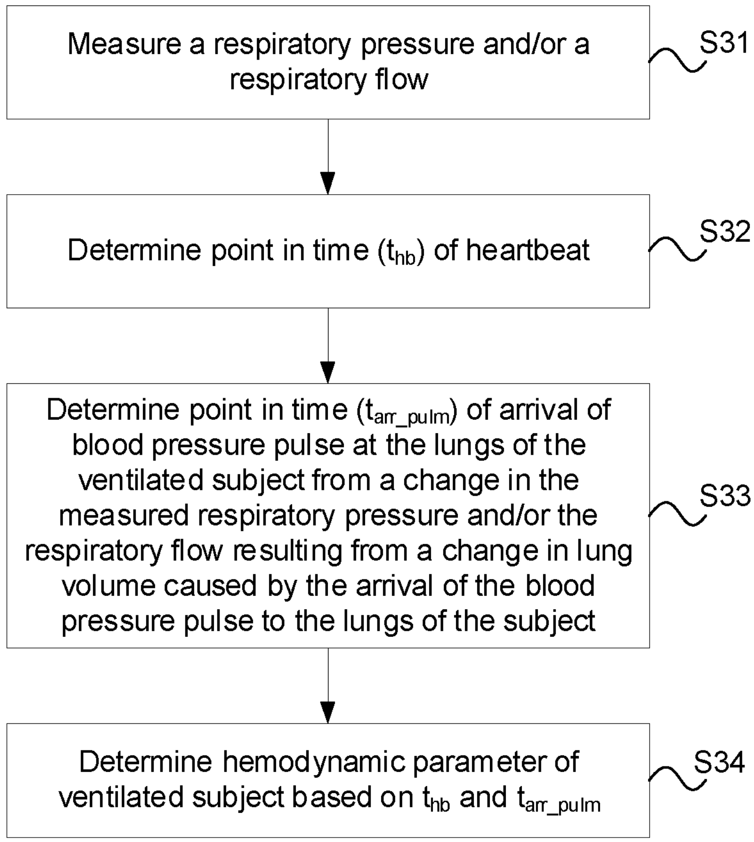
FIGS. 3A-3B is a flowchart illustrating aspects of a method for non-invasive determination of a hemodynamic parameter relating to the pulmonary circulatory system of a mechanically ventilated patient.

FIG. 3A is a flowchart illustrating a method for determining a hemodynamic parameter relating to the pulmonary circulatory system of a mechanically ventilated patient, such as PBP or PCO. The method may be performed by any computerized ventilation system running a computer program comprising instructions that cause the ventilation system and the components thereof to perform the various method steps. When describing the method, simultaneous reference will be made to the exemplary ventilation system 1 in FIG. 1, as well as the diagrams illustrated in FIG. 2.

In a first step, S31, a respiratory pressure and/or a respiratory flow is measured. The respiratory pressure measurements and/or the respiratory flow may be obtained by the one or more pressure sensors 37-37" and/or the one or more flow sensors 33-33".

In a second step, S32, a point in time, $t_{hb}$, of a heartbeat of the ventilated subject 3 is determined. The determination may be made by the control computer 15 of the breathing apparatus 2. The determination may be made based on a change in the measured respiratory pressure and/or respiratory flow, representing a heartbeat-induced cardiogenic oscillation. Optionally, $t_{hb}$ may be determined from an ECG signal captured by the ECG sensor 29 of the ventilation system 1. As described above, blood oxygenation data captured by the blood oxygen sensor 41 may also be used by the control computer 15 to facilitate the determination of $t_{hb}$.

The heartbeat generates a pulmonary blood flow in form of a blood pressure pulse that propagates along the pulmonary arteries towards the lungs of the ventilated subject 3. In a third step, S33, an arrival point in time, $t_{arr\_pulm}$, at which the blood pressure pulse reaches the lungs of the subject is determined. The determination may be made by the control computer 15 and is made based on a change in the measured respiratory pressure and/or respiratory flow, representing a pulmonary-flow induced cardiogenic oscillation resulting from a change in lung volume caused by the arrival of the blood pressure pulse to the lungs of the subject.

In a fourth step, S34, a hemodynamic parameter of the ventilated subject 3 is determined based on the determined point in time, $t_{hb}$, of the heartbeat and the determined point in time, $t_{arr\_pulm}$, of arrival of the blood pressure pulse to the lungs of the subject. The determination may be made by the control computer 15.

Figure 3B:
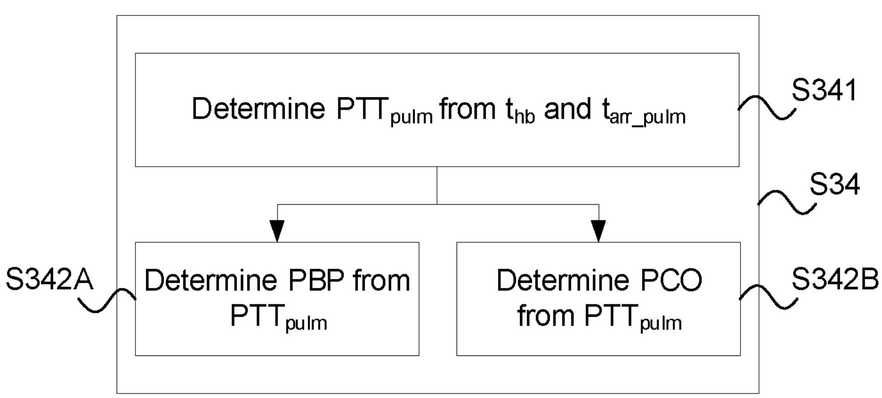

As illustrated in FIG. 3B, step S34 may comprise a step S341 of determining a pulmonary pulse transit time, $PTT_{pulm}$, from $t_{hb}$ and $t_{arr\_pulm}$. $PTT_{pulm}$ may then be used in a subsequent step to determine any or both of PBP (step S342A) or PCO (step S342B), e.g. using the relationships defined by Equations 1 and 2.

Determination of Systemic Blood Pressure (SBP) and Systemic Cardiac Output (SCO)

It should be appreciated that the above-described principles of determining the point in time of the heartbeat, $t_{hb}$, from heartbeat-induced cardiogenic oscillations in the measured respiratory pressure and/or flow may be used independent of the principles of determining a point in time of arrival, $t_{arr\_pulm}$, of the blood pressure pulse to the lungs of the ventilated patient 3 from pulmonary-flow induced cardiogenic oscillations. Determining $t_{hb}$ from respiratory pressure and/or respiratory flow measurements is advantageous, in particular during mechanical ventilation, in that respiratory pressure and flow measurements are readily available from conventional pressure and flow sensors of the ventilation system, and in that no additional equipment is required in the determination.

As shown above, $t_{hb}$ as determined from heartbeat-induced cardiogenic oscillations may be used together with $t_{arr\_pulm}$ to determine a pulmonary PTT, $PTT_{pulm}$, which in turn may be used to determine hemodynamic parameters relating to the pulmonary circulatory system of the ventilated patient, such as PBP and PCO. However, the may also be used together with a point in time of arrival of a blood pressure pulse to a point of arrival in the systemic circulatory system of the ventilated patient 3, so as to determine a systemic PTT which, in turn, can be used to determine hemodynamic parameters relating to the systemic circulatory system of the ventilated patient, such as SBP and SCO.

With reference again made to FIG. 2, the point in time $t_{O2}$ represents the time of detection of a change in blood oxygenation, as measured by the blood oxygen sensor 41. The control computer 15 may be configured to determine a point in time of arrival, denoted $t_{arr\_sys}$, of the blood pressure pulse generated at $t_{hb}$ to a point of arrival in the systemic circulatory system of the patient 3, based on the point in time of detection of the change in blood oxygenation, $t_{O2}$. In the illustrated example, the point of arrival of the blood pressure pulse in the circulatory system of the ventilated patient 3 is hence an artery of the patient's fingertip in which blood oxygenation is measured by the blood oxygen sensor 41.

This point in time of arrival, $t_{arr\_sys}$, may be determined by the control computer 15 to correspond to the point in time of detection of the change in blood oxygenation, $t_{O2}$, or it may be determined as $t_{O2}$ minus a known time delay caused by a measurement delay of the sensor system.

The control computer 15 may then determine the systemic PTT, $PTT_{sys}$, of the blood pressure pulse propagating from the heart of the patient 3 to the point of arrival in the patient's fingertip from $t_{hb}$ and $t_{arr\_sys}$. For example, the control computer 15 may determine $PTT_{sys}$ as the difference between $t_{hb}$ and $t_{arr\_sys}$. The thus determined $PTT_{sys}$ may then be used by the control computer 15 to calculate different hemodynamic parameters relating to the systemic circulatory system of the patient 3.

For instance, the control computer 15 may determine the SBP of the ventilated patient 3 based on the $PTT_{sys}$. According to one example, the control computer 15 may determine the SBP of the ventilated patient 3 based on the relationship $$SBP = -\frac{2}{\alpha}\cdot \ln PTT_{sys} + \frac{\ln\frac{2r\rho L^2}{hE_0}}{\alpha}, \quad \text{(Eq. 3)}$$

where SBP is the systemic blood pressure, $\alpha$ is a constant, $PTT_{sys}$ is the systemic pulse transit time determined in accordance with the above described principles, r is the inner radius of the blood vessel, $\rho$ is the blood density, L is the vessel length, h is the vessel wall thickness, and $E_0$ is the zero-pressure elastic modulus of the vessel wall.

Furthermore, the control computer 15 may determine the SCO of the ventilated patient 3 based on the $PTT_{sys}$. According to one example, the control computer 15 may determine the SCO of the ventilated patient 3 using the esCCO approach, meaning that SCO may be determined based on the relationship $$SCO=K\times(\alpha\times PTT_{sys}+\beta)\times HR \quad \text{(Eq. 4)}$$

where $\alpha$ is a constant, $PTT_{sys}$ is the systemic pulse transit time determined in accordance with the above described principles, K and $\beta$ are constants that are adapted to the ventilated patient 3, and HR is the heartrate of the patient.

From the above, it should be appreciated that the proposed method of determining $t_{hb}$ from a change in the measured respiratory pressure and/or flow, caused by the physical impact of the heart on the lungs of the patient during a heartbeat (i.e. from heartbeat-induced cardiogenic oscillations), may be used to determine parameters relating to both the pulmonary circulatory system and the systemic circulatory system of the ventilated patient, including but not limited to PBP, PCO, SBP and SCO.

Consequently, according to an aspect of the present disclosure, there is provided a method for non-invasive determination of a hemodynamic parameter of a mechanically ventilated subject based on a point in time, $t_{hb}$, of a heartbeat of the subject and an arrival point in time, $t_{arr\_pulm}$ or $t_{arr\_sys}$, at which a blood pressure pulse caused by the heartbeat reaches a point of arrival in the circulatory system of the subject. The method comprises the steps of measuring a respiratory pressure and/or a respiratory flow, and determining the from a change in the measured respiratory pressure and/or the respiratory flow resulting from a physical impact of the heart on the lungs of the subject during the heartbeat.

Figure 4A:
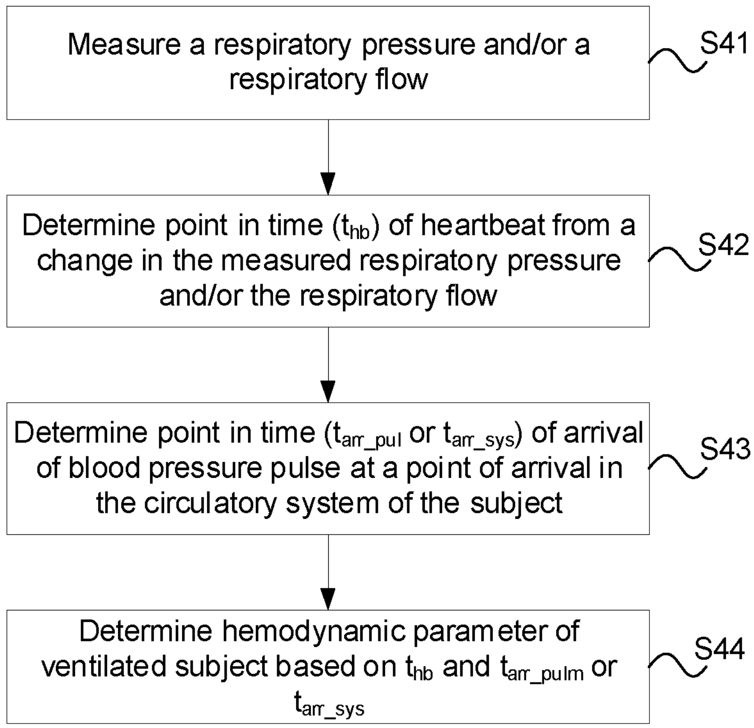
FIGS. 4A-4B is a flowchart illustrating aspects of a method for non-invasive determination of a hemodynamic parameter relating to any of the pulmonary or systemic circulatory system of a mechanically ventilated patient.

FIG. 4A is a flowchart illustrating a method for determining a hemodynamic parameter relating to either the pulmonary circulatory system or the systemic circulatory system of a mechanically ventilated patient, such as PBP, PCO, SBP or SCO. The method may be performed by any computerized ventilation system running a computer program comprising instructions that cause the ventilation system and the components thereof to perform the various method steps. When describing the method, simultaneous reference will be made to the exemplary ventilation system 1 in FIG. 1, as well as the diagrams illustrated in FIG. 2.

In a first step, 41, a respiratory pressure and/or a respiratory flow is measured. The respiratory pressure measurements and/or the respiratory flow may be obtained by the one or more pressure sensors 37-37" and/or the one or more flow sensors 33-33".

In a second step, S42, a point in time, $t_{hb}$, of a heartbeat of the ventilated subject 3 is determined. The determination may be made by the control computer 15 of the breathing apparatus 2. The determination may be made based on a change in the measured respiratory pressure and/or respiratory flow, representing a heartbeat-induced cardiogenic oscillation resulting from a physical impact of the heart on the lungs of the ventilated subject during a heartbeat.

In a third step, S43, an arrival point in time, $t_{arr\_pulm}$ or $t_{arr\_sys}$, at which a blood pressure pulse generated by the heartbeat reaches a point of arrival in the circulatory system of the ventilated subject is determined. The blood pressure pulse may be a pulmonary blood pressure pulse propagating along the pulmonary arteries and arriving at a point of arrival in the pulmonary circulatory system of the subject 3, e.g. at the lungs of the subject. The blood pressure pulse may also be a systemic blood pressure pulse propagating along systemic arteries and arriving at a point of arrival in the systemic circulatory system of the subject 3, e.g. at a point of blood oxygenation measurement in a fingertip of the subject. The point in time of arrival may be determined based on a change in a monitored parameter, which change is indicative of the arrival of the blood pressure pulse to the point of arrival. When determining the point in time of arrival of a pulmonary blood pressure pulse to a point of arrival in the pulmonary circulatory system of the subject, the determination may, for instance, be made based on a change in the measured respiratory pressure and/or respiratory flow, representing a pulmonary-flow induced cardiogenic oscillation resulting from a change in lung volume caused by the arrival of the blood pressure pulse to the lungs of the subject. When determining the point in time of arrival of a systemic blood pressure pulse to a point of arrival in the systemic circulatory system of the subject, the determination may, for instance, be made based on a change in blood oxygenation at a point of measurement in the systemic circulatory system of the subject 3.

In a fourth step, S44, a hemodynamic parameter of the ventilated subject 3 is determined based on the determined point in time, $t_{hb}$, of the heartbeat and the determined point in time, $t_{arr\_pulm}$ or $t_{arr\_sys}$, of arrival of the blood pressure pulse to the point of arrival in the circulatory system of the subject.

If the blood pressure pulse is a pulmonary blood pressure pulse arriving at a point of arrival in the pulmonary circulatory system of the subject, step S44 corresponds to step S34 in FIG. 3. In this case, the determination of the hemodynamic parameter may comprise the steps of determining a pulmonary pulse transit time, $PTT_{pulm}$, from $t_{hb}$ and $t_{arr\_pul}$ (corresponding to step S341 in FIG. 3) and determining any or both of PBP and PCO from $PTT_{pulm}$ (corresponding to steps S342A and S342B in FIG. 3).

Figure 4B:
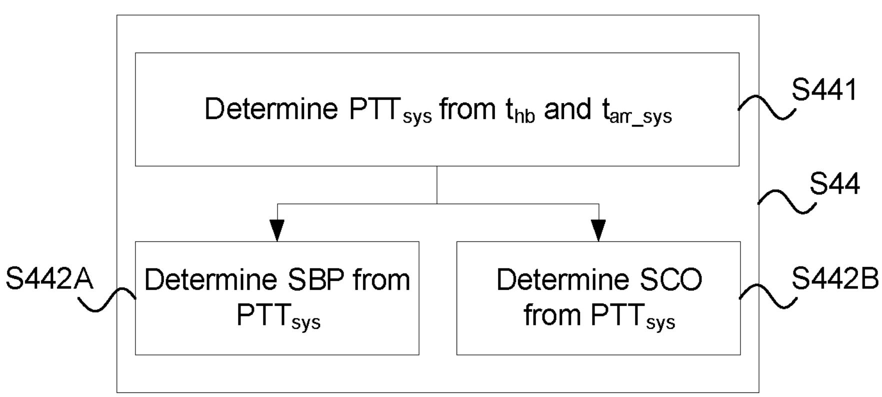

If the blood pressure pulse is a systemic blood pressure pulse arriving at a point of arrival in the systemic circulatory system of the subject, step S44 may comprise the steps illustrated in FIG. 4B. In this case, a systemic pulse transit time, $PTT_{sys}$, may be determined from the and $t_{arr\_sys}$ (step S441), whereby $PTT_{sys}$ may be used to determine any or both of SBP (step S442A) or SCO (step S442B), e.g. using the relationships defined by Equations 3 and 4.

Determination of Cardiac Shunt

The control computer 15 may further be configured to determine a cardiac shunt of the ventilated patient 3 based on a relationship between the PCO and the SCO of the patient, where any or both of PCO and SCO is determined using the principles described above. The cardiac shunt of the patient 3 may, for example, be determined as the difference between SCO and PCO.

The cardiac shunt of the ventilated patient 3 may be advantageously used in the diagnosis of ventricular septal defect (VSD). About 2-3 per thousand people are born with VSD, which is a defect in the ventricular septum, the wall dividing the left and right ventricles of the heart, causing a cardiac shunt flow from the left ventricle into the right ventricle.

Diagnosis of VSD is a non-trivial task typically requiring invasive and/or expensive medical equipment. However, the proposed method for cardiac shunt determination enables diagnosis of VSD to be performed non-invasively with a minimum of additional equipment.

Furthermore, most known techniques for VSD diagnosis (except for imaging techniques such as cardiac CT and MRI) will fail to detect a VSD if, at the time of examination of the patient, the patient is in a physiological state at which no cardiac shunt is generated. An advantage of the proposed method for cardiac shunt determination during mechanical ventilation is that, in case of VSD, cardiac shunt can be provoked by exposing the pulmonary system of the patient to an increased level of pulmonary stress by altering the ventilation settings of the breathing apparatus.

For example, the control computer 15 may be configured to determine a first value of cardiac shunt of the patient 3 based on SCO and PCO values determined during ventilation of the patient using a first set of ventilation settings causing a first respiratory pressure to be applied to the patient, and to determine a second value of cardiac shunt of the patient 3 based on SCO and PCO determined during ventilation of the patient using a second set of ventilation settings causing a second and different respiratory pressure to be applied to the patient. The control computer may then be configured to determine if the patient 3 suffers from VSD based on a difference between the first and the second cardiac shunt values. In other words, the control computer 15 may be configured to determine if the ventilated patient 3 suffers from VSD based on a change in cardiac shunt resulting from a change in a respiratory pressure applied to the patient.

Figure 5:
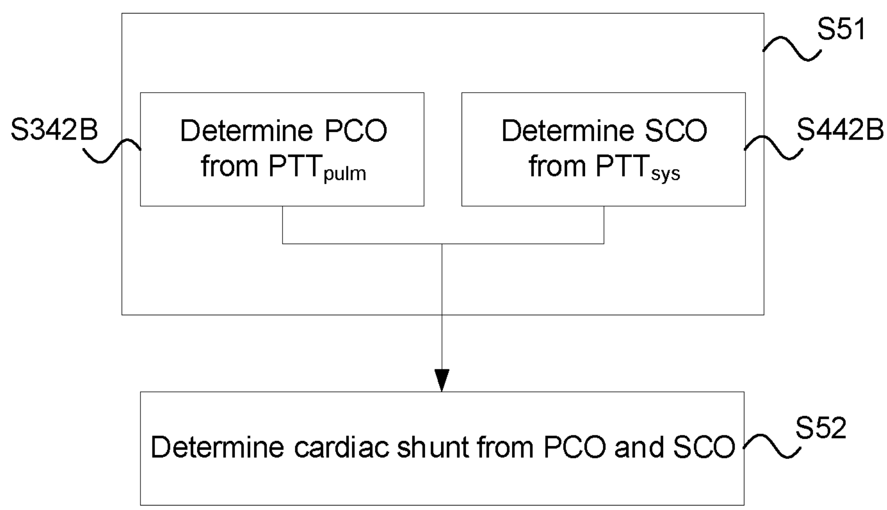
FIG. 5 is a flowchart illustrating further aspects of a method for non-invasive determination of a hemodynamic parameter of a mechanically ventilated patient.

Consequently, according to another aspect of the present disclosure, there is provided a method for non-invasive determination of a cardiac shunt a mechanically ventilated subject based on a relationship between the PCO and the SCO of the subject, wherein any or both of PCO and SCO is determined using the above described principles. As illustrated in FIG. 5, the method comprises a step S51 of determining PCO and SCO, and a step S52 of determining the cardiac shunt of the ventilated subject from PCO and SCO. The PCO used in the cardiac shunt determination may, for instance, be the PCO determined in step S342B (see FIG. 3B), and the SCO used in the cardiac shunt determination may, for instance, be the SCO determined in step S442B (see FIG. 4B).

Although the proposed methods of non-invasive determination of hemodynamic parameters have been described above as being performed by the control computer 15 of the breathing apparatus 2 providing the mechanical ventilation to the patient 3, it should be appreciated that the method may just as well be performed by any other apparatus capable of obtaining measurements of respiratory pressure and/or respiratory flow. For example, the method may be performed by a patient monitor connected to al flow sensor for obtaining respiratory flow measurements during ongoing ventilatory treatment of the monitored patient. Such a flow-sensor equipped patient monitor may store the computer program described above, and be caused to perform any of the described methods upon execution of the computer program by a computer of the patient monitor. Likewise, the proposed methods may be performed by a stand-alone computer, such as a personal computer (PC), configured to receive respiratory pressure and/or respiratory flow measurements from a pressure and/or flow sensor of the ventilation system 1.

The invention claimed is:

1. A method for non-invasive determination of a hemodynamic parameter of a subject mechanically ventilated via a breathing apparatus based on a point in time ($t_{hb}$) of a heartbeat of the subject and an arrival point in time ($t_{arr\_pulm}$, $t_{arr\_sys}$) at which a blood pressure pulse caused by the heartbeat reaches a point of arrival in a circulatory system of the subject, comprising:

obtaining a respiratory pressure and/or a respiratory flow via one of a pressure sensor and a flow sensor, respectively;

estimating a time window for a heartbeat based on data obtained from a blood oxygen sensor;

determining, within the time window, the point in time ($t_{hb}$) of the heartbeat from a change in the measured respiratory pressure and/or the respiratory flow resulting from a physical impact of the heart on the lungs of the subject during the heartbeat;

determining, via a controller of the breathing apparatus:

a pulmonary pulse transit time, $PTT_{pulm}$, for the blood pressure pulse based on the point in time of the heartbeat ($t_{hb}$) and a point in time of arrival ($t_{arr\_pulm}$) of the blood pressure pulse to the lungs of the subject; and/or a systemic pulse transit time, $PTT_{sys}$, for the blood pressure pulse based on the point in time of the heartbeat ($t_{hb}$) and a point in time of arrival ($t_{arr\_sys}$) of the blood pressure pulse to a point of arrival in the systemic circulatory system of the subject; and determining, via the controller, the hemodynamic parameter based on $PTT_{pulm}$ and/or $PTT_{sys}$.

2. The method of claim 1, wherein the point in time of the heartbeat ($t_{hb}$) is determined from a change in magnitude of the measured respiratory pressure and/or the respiratory flow.

3. The method of claim 1, wherein the point in time of the heartbeat ($t_{hb}$) is determined from a change in a first and/or second order derivative with respect to time of the measured respiratory pressure and/or the measured respiratory flow.

4. The method of claim 1, further comprising:

estimating a time window ($\Delta T_{hb(P)}$) for the heartbeat based on at least one parameter indicative of an approximate point in time of the heartbeat, and determining the point in time of the heartbeat ($t_{hb}$) based on the respiratory pressure and/or respiratory flow measured during the estimated time window.

5. The method of claim 4, wherein the time window ($\Delta T_{hb(P)}$) is estimated based on any of, or any combination of:

blood oxygenation data relating to oxygenation of blood in a body part at a known or assumable distance from the heart of the subject;

systemic blood pressure data relating to a systemic blood pressure measured in a body part at a known or assumable distance from the heart of the subject;

the determined arrival point in time ($t_{arr\_pulm}$, $t_{arr\_sys}$) of the blood pressure pulse to the lungs of the subject;

the point(s) in time of one or more previous heartbeats, and the point(s) in time of arrival at the lungs of the subject of one or more previous blood pressure pulses generated by the one or more previous heartbeats.

6. The method of claim 1, further comprising:

determining the arrival point in time ($t_{arr\_pulm}$, $t_{arr\_sys}$) as a point in time of arrival ($t_{arr\_pulm}$) of the blood pressure pulse to the lungs of the subject from a change in the measured respiratory pressure and/or the respiratory flow resulting from a change in lung volume caused by the arrival of the blood pressure pulse to the lungs of the subject.

7. The method of claim 6, further comprising:

estimating a time window for the arrival of the blood pressure pulse to the lungs of the subject based on at least one parameter indicative of an approximate point in time of arrival of the blood pressure pulse to the lungs of the subject, and determining the point in time of arrival ($t_{arr\_pulm}$) based on the respiratory pressure and/or respiratory flow measured during the estimated time window.

8. The method of claim 6, wherein the time window is estimated based on any of, or any combination of:

the point in time ($t_{hb}$) of the heartbeat;

the point(s) in time of one or more previous heartbeats; and the point(s) in time of arrival at the lungs of the subject of one or more previous blood pressure pulses generated by the one or more previous heartbeats.

9. The method of claim 1, further comprising:

determining a pulmonary blood pressure, PBP, of the subject or a pulmonary cardiac output, PCO, of the subject as the hemodynamic parameter, based on $PTT_{pulm}$.

10. The method of claim 1, further comprising:

measuring a blood oxygenation at a point of blood oxygenation measurement in the systemic circulatory system of the subject; and determining the point in time of arrival ($t_{arr\_sys}$) of the blood pressure pulse to a point of arrival in the systemic circulatory system as a point in time of arrival of the blood pressure pulse to the point of blood oxygenation measurement, based on a change in the measured blood oxygenation.

11. The method of claim 1, further comprising:

determining a systemic blood pressure, SBP, of the subject or a systemic cardiac output, SCO, of the subject as the hemodynamic parameter, based on $PTT_{sys}$.

12. The method of claim 1, further comprising:

determining a cardiac shunt of the ventilated subject based on a relationship between a system cardiac output, SCO, and a pulmonary cardiac output, PCT, of the subject, wherein PCO is determined based on $PTT_{pulm}$ and/or SCO is determined based on $PTT_{sys}$.

13. A computer program product for non-invasive determination of a hemodynamic parameter of a subject mechanically ventilated via a breathing apparatus based on a point in time ($t_{hb}$) of a heartbeat of the subject and an arrival point in time ($t_{arr\_pulm}$, $t_{arr\_sys}$) at which a blood pressure pulse caused by the heartbeat reaches a point of arrival in a circulatory system of the subject, the computer program product comprising a non-transitory computer-readable data storage medium storing instructions which, when executed by a computer, causes the computer to perform the steps of claim 1.

14. A ventilation system for non-invasive determination of a hemodynamic parameter of a mechanically ventilated subject based on a point in time ($t_{hb}$) of a heartbeat of the subject and an arrival point in time ($t_{arr\_pulm}$, $t_{arr\_sys}$) at which a blood pressure pulse caused by the heartbeat reaches a point of arrival in a circulatory system of the subject, the ventilation system comprising:

a breathing apparatus mechanically ventilating the subject;

at least one pressure sensor measuring a respiratory pressure and/or at least one flow sensor measuring a respiratory flow;

a blood oxygen sensor; and a computer determining the hemodynamic parameter, wherein the computer is configured to:

estimate a time window for a heartbeat based on data obtained from the blood oxygen sensor;

determine, within the time window, the point in time ($t_{hb}$) of the heartbeat from a change in the measured respiratory pressure and/or the respiratory flow resulting from a physical impact of the heart on the lungs of the subject during the heartbeat;

determine:

a pulmonary pulse transit time, $PTT_{pulm}$, for the blood pressure pulse based on the point in time of the heartbeat ($t_{hb}$) and a point in time of arrival ($t_{arr\_pulm}$) of the blood pressure pulse to the lungs of the subject; and/or a systemic pulse transit time, $PTT_{sys}$, for the blood pressure pulse based on the point in time of the heartbeat ($t_{hb}$) and a point in time of arrival ($t_{arr\_sys}$) of the blood pressure pulse to a point of arrival in the systemic circulatory system of the subject; and determine the hemodynamic parameter based on $PTT_{pulm}$ and/or $PTT_{sys}$.

15. The ventilation system of claim 14, wherein the computer is configured to determine the point in time of the heartbeat ($t_{hb}$) from a change in magnitude of the measured respiratory pressure and/or the respiratory flow.

16. The ventilation system of claim 14, wherein the computer is configured to determine the point in time of the heartbeat ($t_{hb}$) from a change in a first and/or second order derivative with respect to time of the measured respiratory pressure and/or the measured respiratory flow.

17. The ventilation system of claim 14, wherein the computer is configured to estimate a time window ($\Delta T_{hb(P)}$) for the heartbeat based on at least one parameter indicative of an approximate point in time of the heartbeat, and determining the point in time of the heartbeat ($t_{hb}$) based on the respiratory pressure and/or respiratory flow measured during the estimated time window.

18. The ventilation system of claim 17, wherein the computer is configured to estimate the time window ($\Delta T_{hb(P)}$) based on any of, or any combination of:

blood oxygenation data relating to oxygenation of blood in a body part at a known or assumable distance from the heart of the subject;

systemic blood pressure data relating to a systemic blood pressure measured in a body part at a known or assumable distance from the heart of the subject;

the determined arrival point in time ($t_{arr\_pulm}$, $t_{arr\_sys}$) of the blood pressure pulse to the lungs of the subject;

the point(s) in time of one or more previous heartbeats, and the point(s) in time of arrival at the lungs of the subject of one or more previous blood pressure pulses generated by the one or more previous heartbeats.

19. The ventilation system of claim 14, wherein the computer is configured to determine the arrival point in time ($t_{arr\_pulm}$, $t_{arr\_sys}$) as a point in time of arrival ($t_{arr\_pulm}$) of the blood pressure pulse to the lungs of the subject from a change in the measured respiratory pressure and/or the respiratory flow resulting from a change in lung volume caused by the arrival of the blood pressure pulse to the lungs of the subject.

20. The ventilation system of claim 19, wherein the computer is configured to estimate a time window for the arrival of the blood pressure pulse to the lungs of the subject based on at least one parameter indicative of an approximate point in time of arrival of the blood pressure pulse to the lungs of the subject, and determining the point in time of arrival ($t_{arr\_pulm}$) based on the respiratory pressure and/or respiratory flow measured during the estimated time window.

21. The ventilation system of claim 20, wherein the computer is configured to estimate the time window based on any of, or any combination of:

the point in time ($t_{hb}$) of the heartbeat;

the point(s) in time of one or more previous heartbeats; and the point(s) in time of arrival at the lungs of the subject of one or more previous blood pressure pulses generated by the one or more previous heartbeats.

22. The ventilation system of claim 14, wherein the computer is configured to determine a pulmonary blood pressure, PBP, of the subject or a pulmonary cardiac output, PCO, of the subject as the hemodynamic parameter, based on $PTT_{pulm}$.

23. The ventilation system of claim 14, wherein the computer is configured to:

obtain blood oxygenation measurements obtained at a point of blood oxygenation measurement in the systemic circulatory system of the subject, and determine the point in time of arrival ($t_{arr\_sys}$) of the blood pressure pulse to a point of arrival in the systemic circulatory system as a point in time of arrival of the blood pressure pulse to the point of blood oxygenation measurement, based on a change in the measured blood oxygenation.

24. The ventilation system of claim 14, wherein the computer is configured to determine a systemic blood pressure, SBP, of the subject or a systemic cardiac output, SCO, of the subject as the hemodynamic parameter, based on $PTT_{sys}$.

25. The ventilation system of claim 14, wherein the computer is configured to determine a cardiac shunt of the mechanically ventilated subject based a relationship between a systemic cardiac output, SCO, and a pulmonary cardiac output, PCO, of the subject, wherein the computer is configured to determine PCO based on $PTT_{pulm}$ and/or to determine SCO based on $PTT_{sys}$.

* * * * *